United States Patent [19]
Hamilton et al.

[11] Patent Number: 5,770,380
[45] Date of Patent: Jun. 23, 1998

[54] SYNTHETIC ANTIBODY MIMICS—MULTIPLE PEPTIDE LOOPS ATTACHED TO A MOLECULAR SCAFFOLD

[75] Inventors: Andrew D. Hamilton; Yoshitomo Hamuro, both of Pittsburgh, Pa.

[73] Assignee: University of Pittsburgh, Pittsburgh, Pa.

[21] Appl. No.: 712,521

[22] Filed: Sep. 13, 1996

[51] Int. Cl.$^6$ .............................. G01N 33/53; C07K 5/02
[52] U.S. Cl. .......................... 435/7.1; 436/501; 530/300; 530/317; 530/345
[58] Field of Search .............................. 435/7.1; 436/501; 530/300, 317, 345

[56] References Cited

PUBLICATIONS

Linnane P, et al, (1994) Calixarenes: adaptable hosts par excellence. Chemistry.and Industry. 20:811, 1994.
Nigam et al., "Potent Inhibition of Human Tumor p21$^{ras}$ Earnesyltransferase by A$_1$A$_2$–lacking p21$^{ras}$ CA$_1$A$_2$X Peptidomimetics" The Journal of Biological Chemistry Oct. 5, 1993, pp. 20695–20698.
Carell et al., "A Solution–Phase Screening Procedure for the Isolation of Active Compounds from a Library of Molecules" 1994, pp. 2061–2064.
Cholthia et al. "Conformation of Immunogolobulin Hypervariable Regions" Nature vol. 342 21/28 Dec. 1989.
M.L. Smuthe and M. von Itzstein "Design and Synthesis of a Biologically Active Antibody Mimic Based on an Antibody–Antigen Crystal Structure" J. Am. Chem. Soc. 1994 116 2725–2733.
Scarr, et al. Peptide Research "Improved Synthesis and Aminoacylation of p–Nitrobenzophenone Oxime Polystyrene Resin for Solid–Phase Synthesis of Protected Peptides".
Brown et al. "Selective Reductions. XVIII. The Fast Reaction of Primary, Secondary, and Tertiary Amides with Diborane. A Simple Convenient Procedure for the Conversion of Amides to the Corresponding Amines" J. Org. Chem., vol. 38, No. 5, 1975.
Jackson, et al. "Template–Constrained Cyclic Peptides: Design of High–Affinity Ligands for GPIIb/IIIa" J.Am-.Chem.Soc. 1994, 3220–3230.
Chu–Biao Xue et al. "An Efficient Synthesis of Glycoprotein IIb/IIIa Inhibitor DMP728. A Novel Synthesis of No. Methylarginine–Containing Peptides" J.Org.Chem.1995,60, 946–952.
Bushnell et al. "High–Resolution Three–Dimensional Structure of Horse Heart Cytochrome c" J. Mol. Biol. 1990, 214, 585–595.
Conner et al. Synthesis and Alkali Metal Binding Properties of 'Upper Rim' Functionalized Calix[4]arenes[1] Jn.Org.Chem.1992,57,13, 3744–3746.
Vreekamp, R.H. thesis "Calix[4]arene Carboxylic Acids and Calix [4] arene pyridines"University Twente 1995.
Guische et al. "Calixarenes 12 The Synthesis of Functionalized Calixarenes" I. vol. 42 No. 6, pp. 1633–1640, 1986.
Gutsche et al. "Calixarenes. 18. Synthesis Procedures for p–tert Butylcalix[4]arene" J.Org.Chem. 1986 742–745.
The Practice of Peptide Synthesis 2nd ed. 104–105; 114–115.
Satterlee et al. "A proton NMR study of the Non–Covalent Complex of Horse Cytochrome c and Yeast Cytochrome c peroxidase and its Comparison with other Interacting Protein Complexes" Btophvmd 912 1987 87–97.
Terwilligert et al. "The Structure of Melittin" J.Bio. Chem. vol. 257, No. 11 1982 6016–6022.
Dufourcq et al. "Intrinsic Fluorescence Study of Lipid–Protein Interactions in Membrane Models" Biochimica 467 1977 11.
Tooze "Antibody Mimics" Introduction of Protein Structure p. 187.
Young "Solid Phase Peptide Synthesis" 1984 2nd Ed. Pierce Chemical Co., Rockford IL pp. 106, 107.
Carell et al. "A Novel Procedure for the Synthesis of Libaries Containing Small Organic Molecules" Angew.Chem. Int. Ed. Engl. 1994 33 No. 20.
Bach, et al. Structural Studies of a Family of High Affinity Ligands for GPIIb/IIIa J. Am. Chem. Soc. 1994 116 3207–3219.
Hsieh–Wilson et al. "Lessons from the Immune System: From Catalysis to Materials Science" Acc. Chem. Res. 1996 29, 164–170.
Wilson et al. "Structural Aspects of Antibodies and Antibody Antigen Complexes".
Alzari et al. "Three–Dimensional Structure of Antibodies" Am. Rev. Immunol. 1988 6 555–80.

*Primary Examiner*—Lora M. Green
*Assistant Examiner*—Neal A. Musto
*Attorney, Agent, or Firm*—Michael J. Kline, Esq.

[57] ABSTRACT

A synthetic antibody mimic comprising multiple peptide loops built on an organic or molecular scaffold. In a highly preferred embodiment of the invention, a calixarene unit comprises the organic scaffold to which is attached a plurality of peptide loops. The antibody mimics allow for the generation of large libraries of artificial antibodies that can be screened for binding to target antigens.

15 Claims, 14 Drawing Sheets

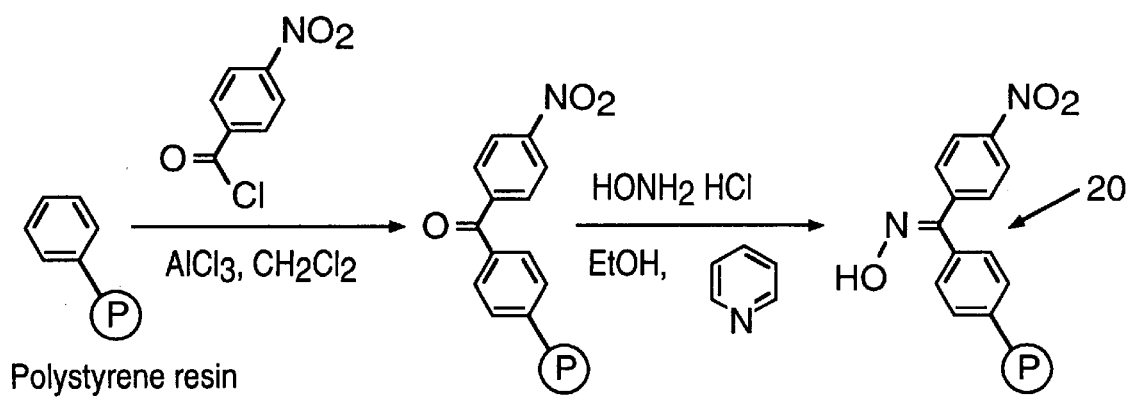
FIG. 1A  Synthesis of Oxime Resin
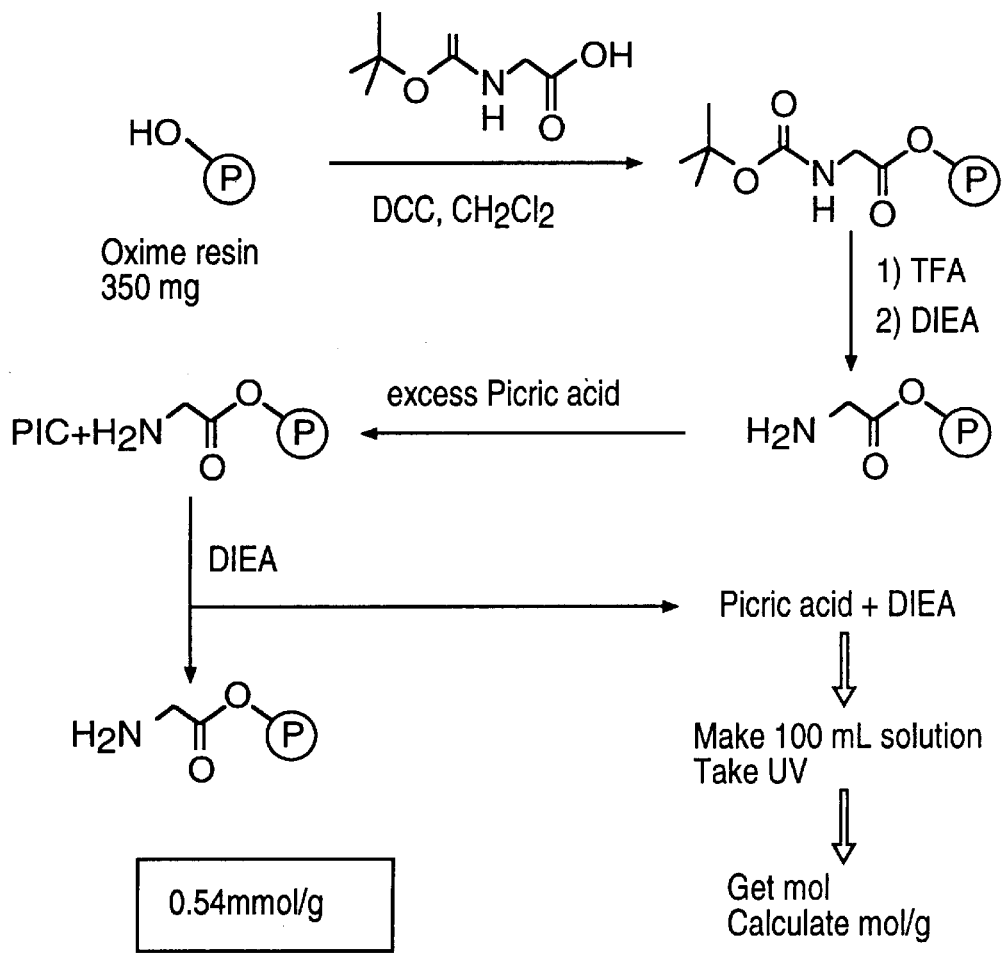
FIG. 1B  Checking the Substitution Level

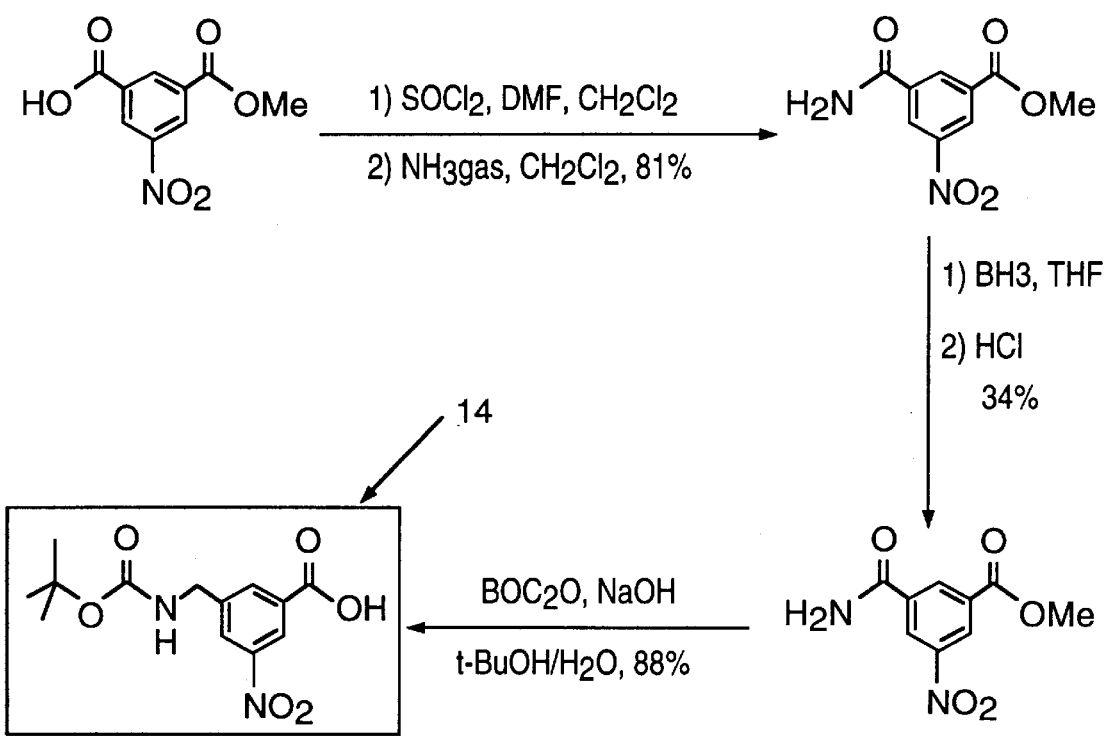
FIG. 1C  Synthesis of Spacer

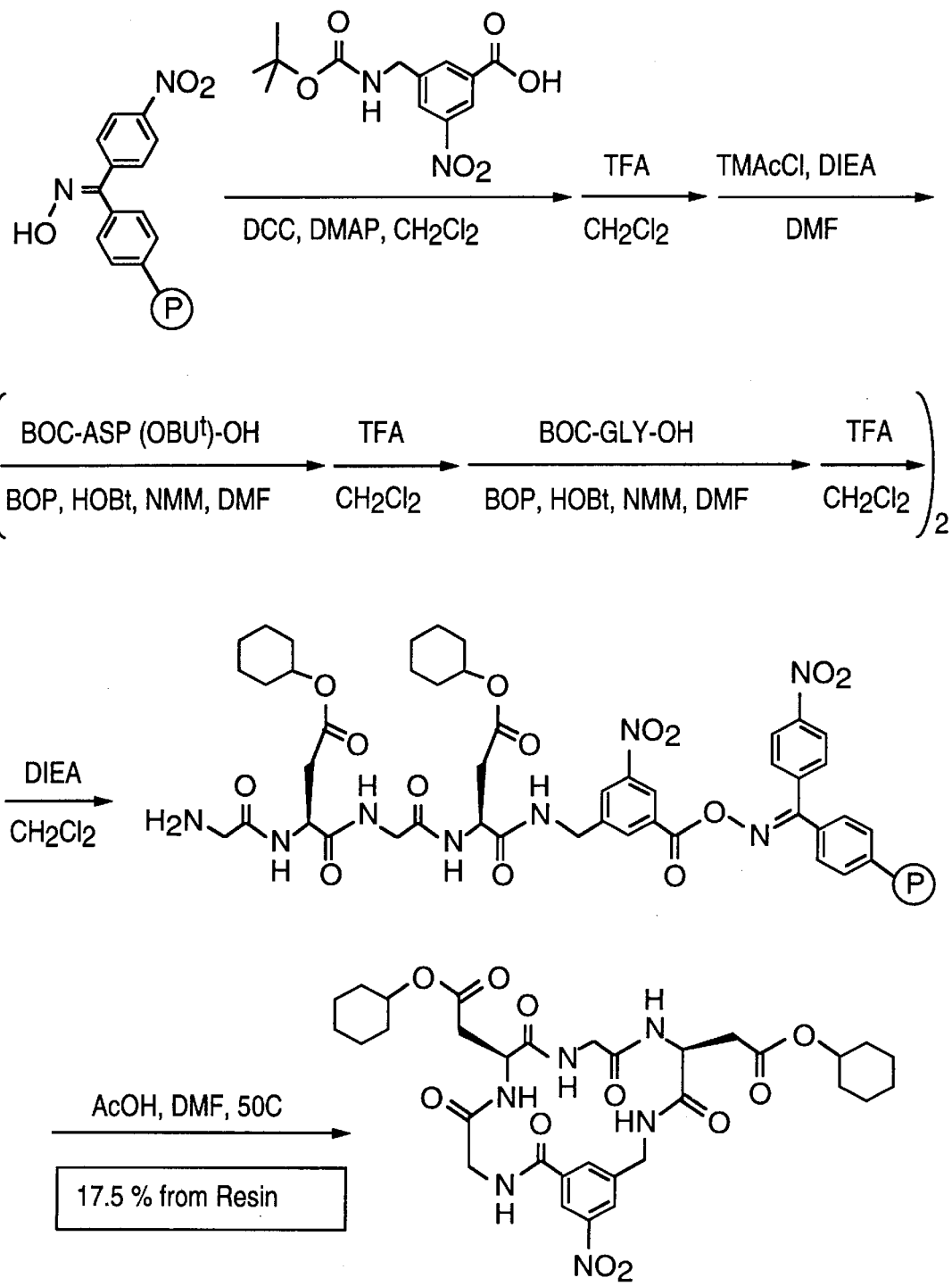
FIG. 1D  Solid Phase Peptide Synthesis

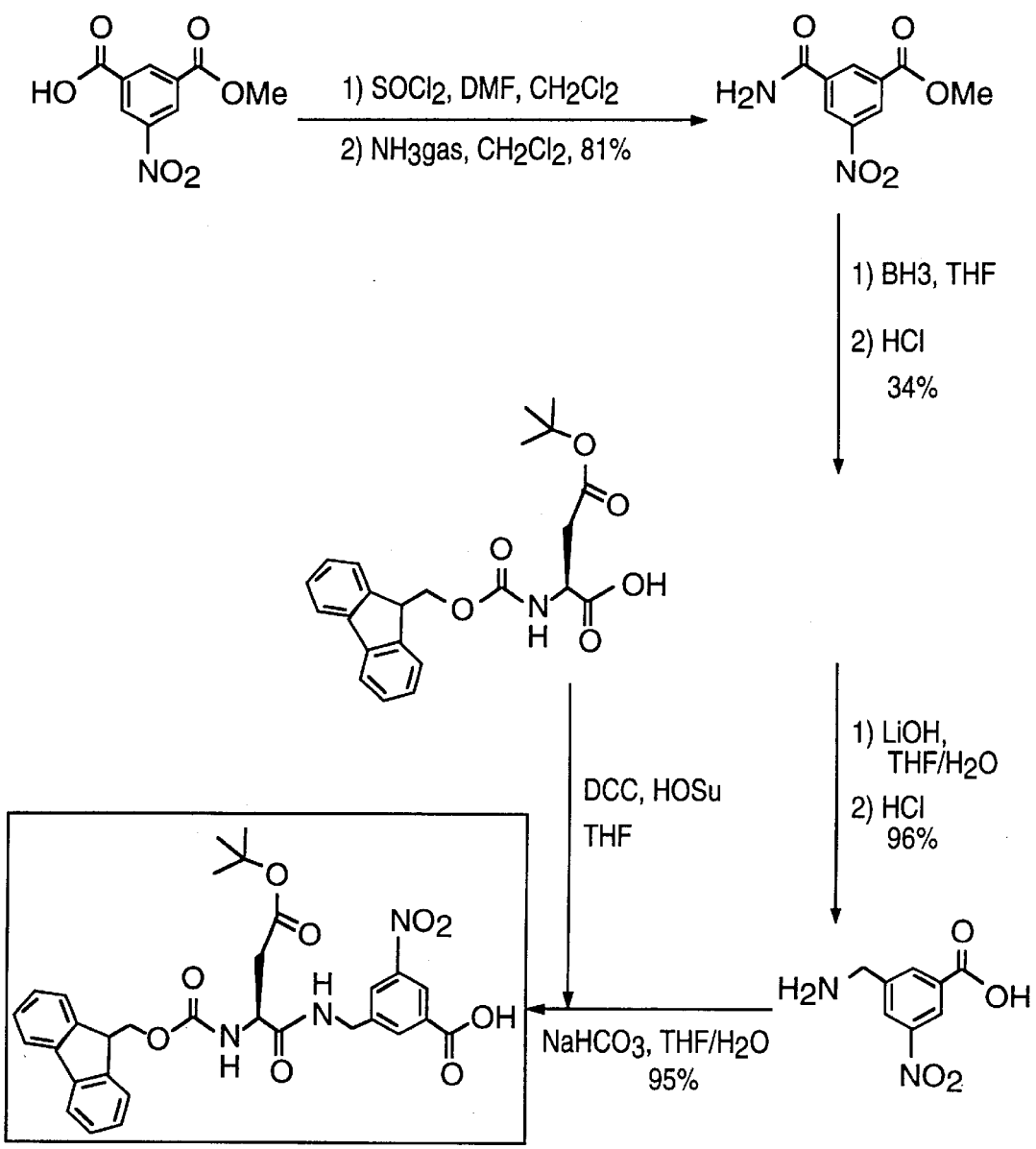
FIG. 2A  Synthesis of First Fragment

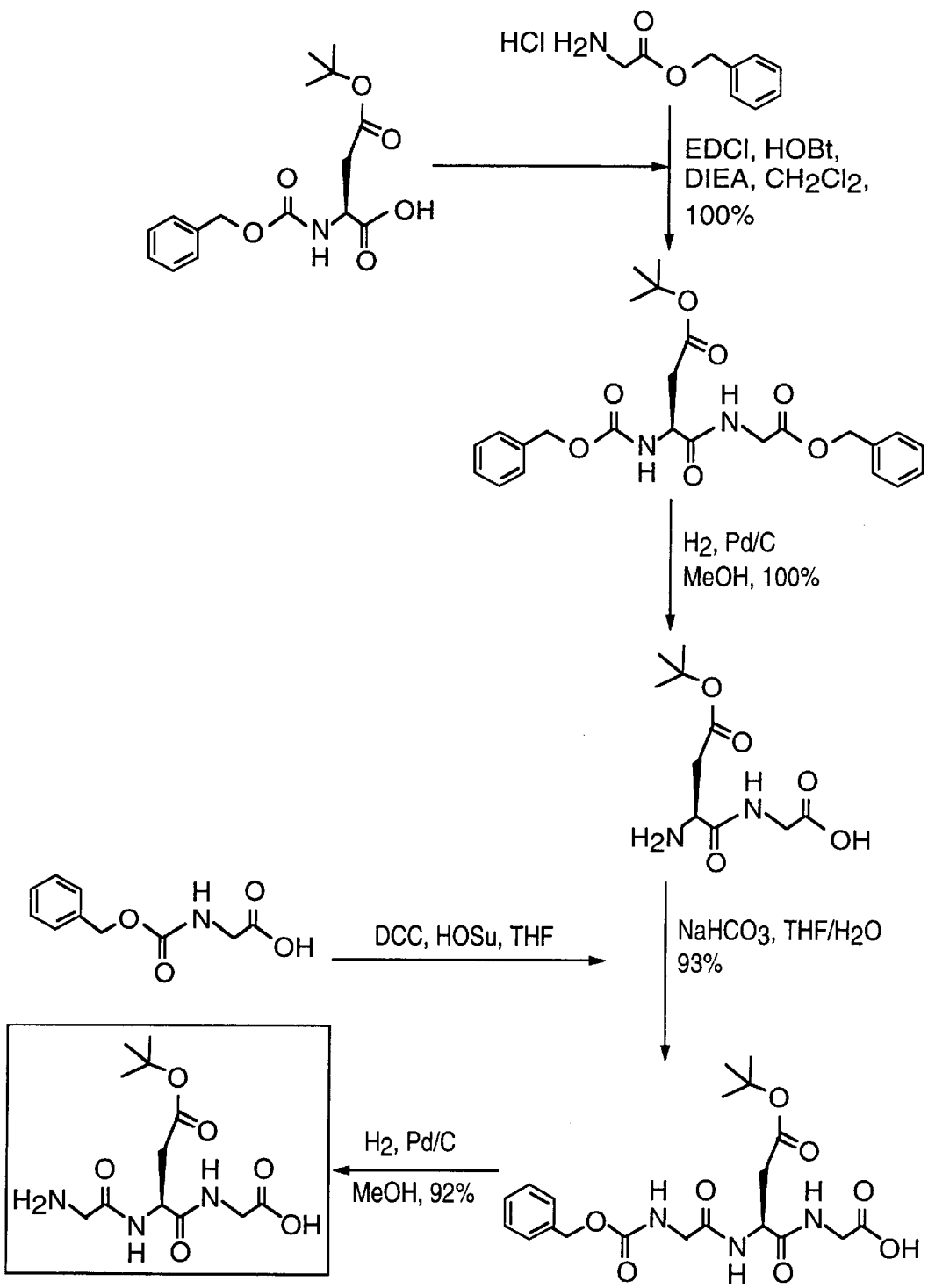
FIG. 2B  Synthesis of Second Fragment

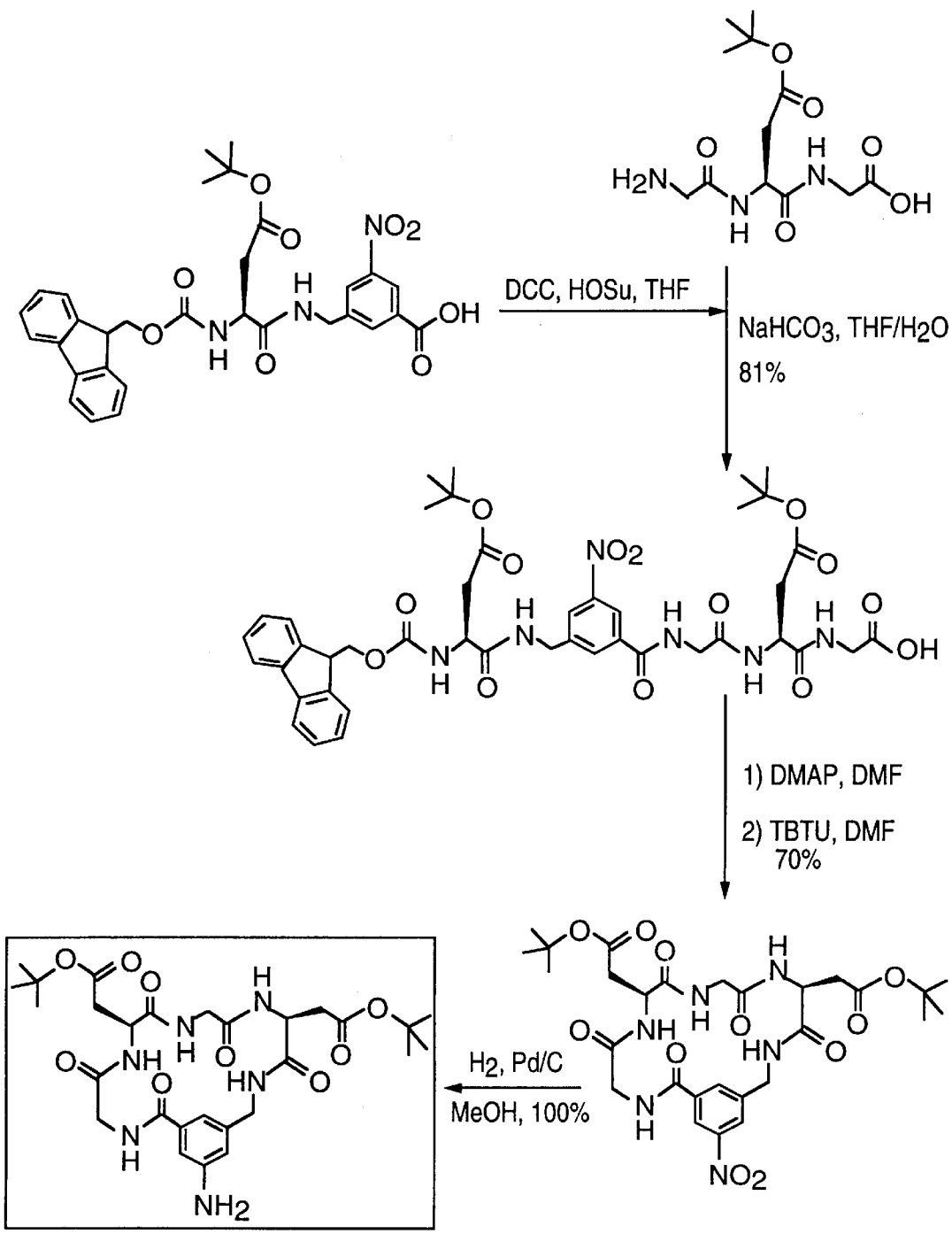
FIG. 2C  Synthesis of Cyclic Peptide

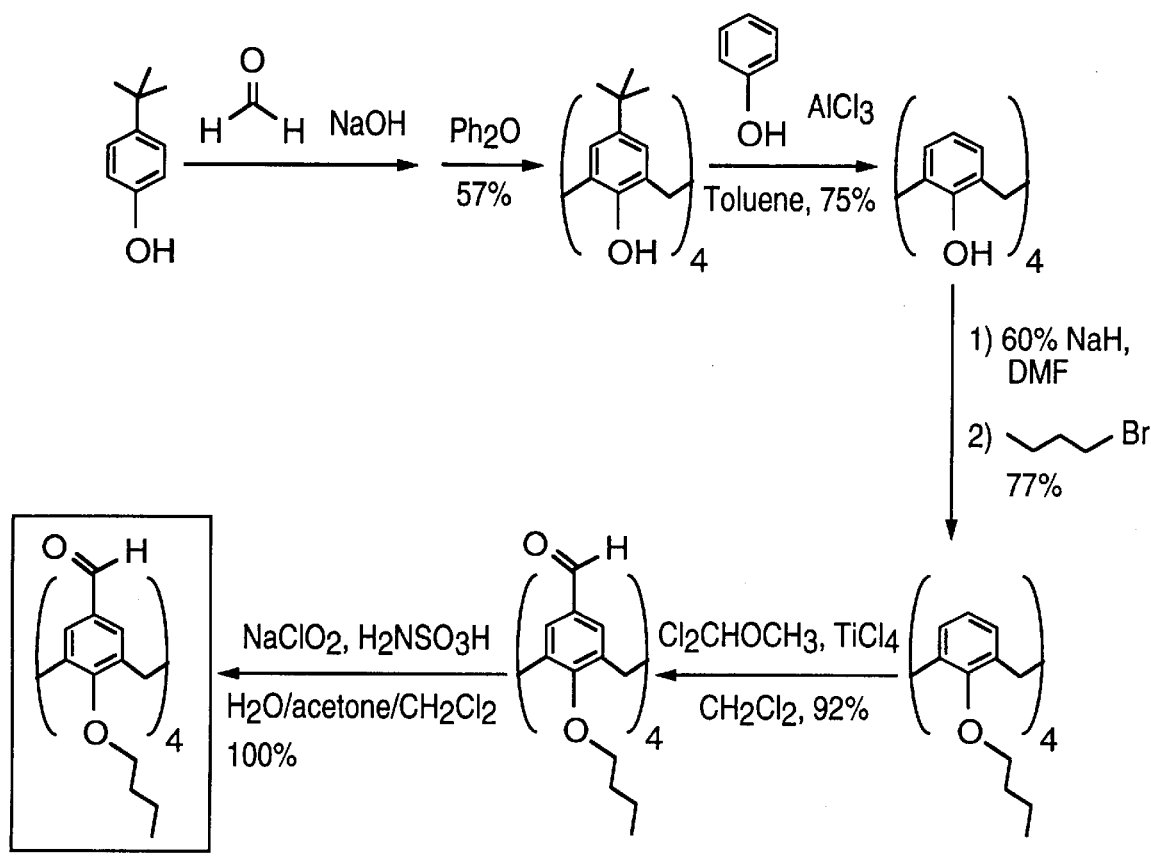
FIG. 3  Synthesis of Calix[4] arenetetraacid

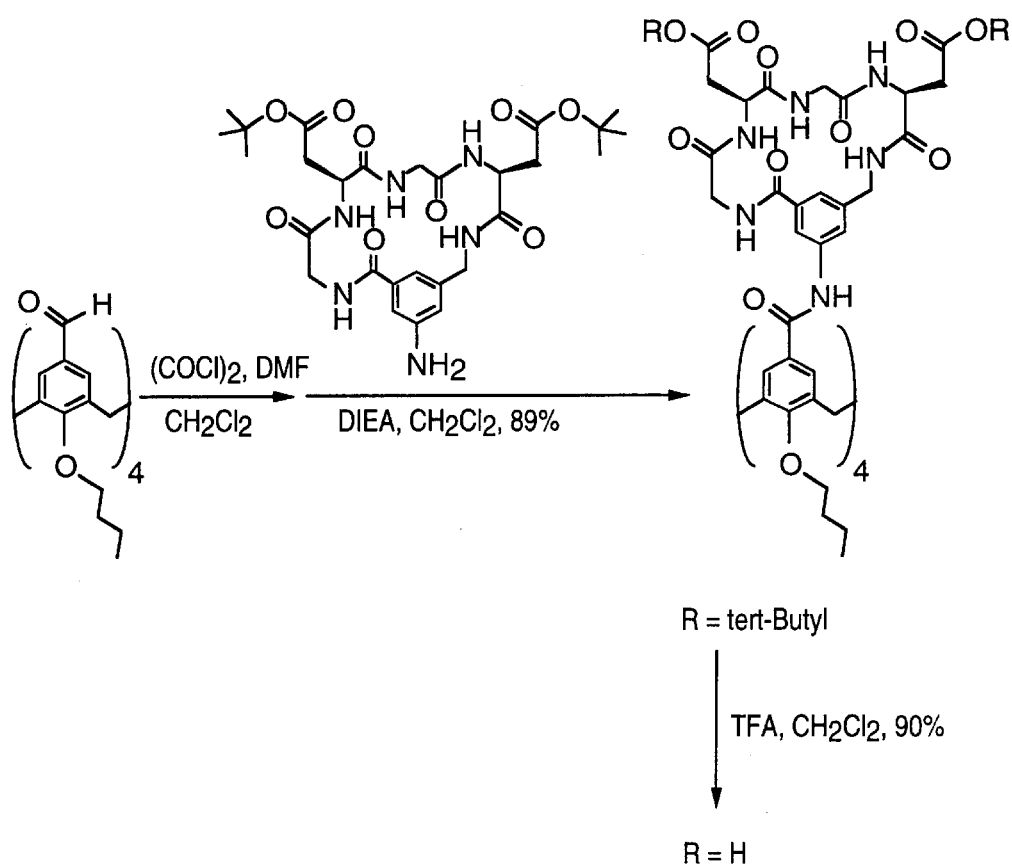
FIG. 4  Synthesis of Calixarene Cyclic Peptide

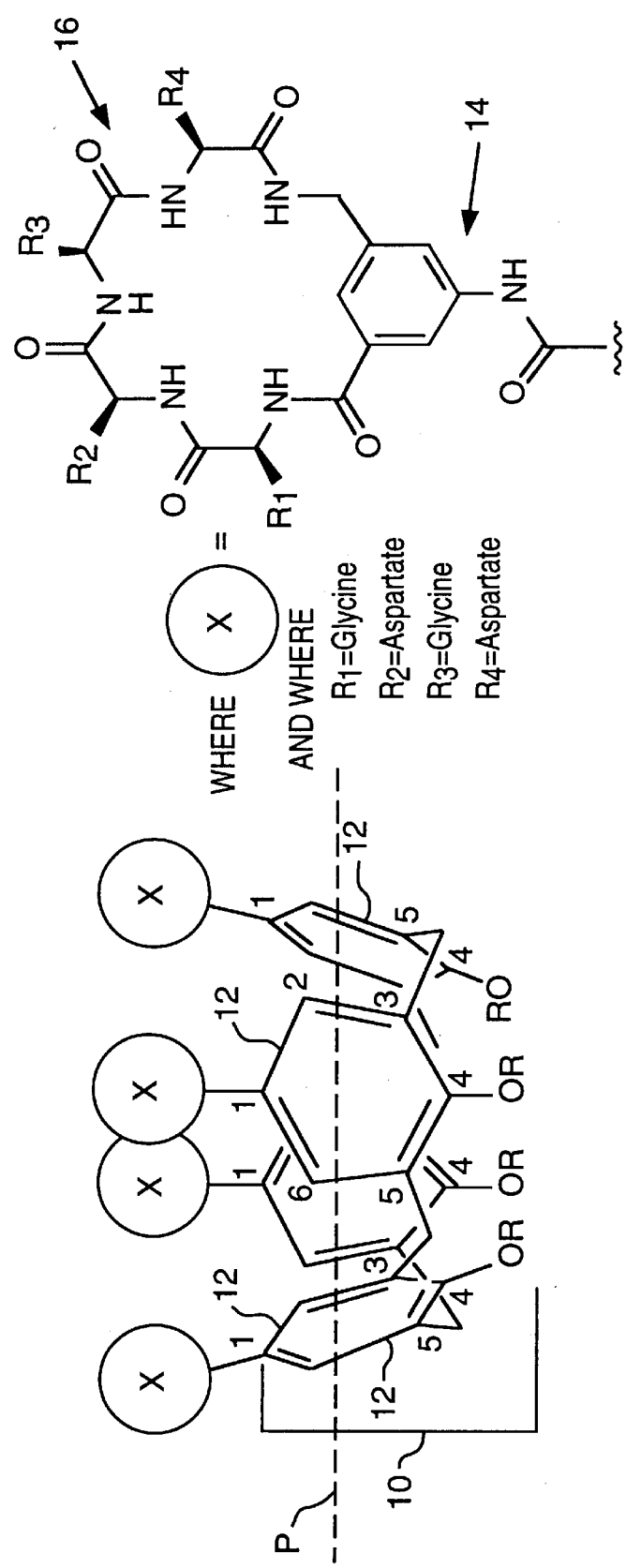
FIG. 5 Design of synthetic antibody mimics based on a calixarene scaffold.

NMR Titration of 3.0 mM Cytochrome c with 1 in 12 mM $KNO_3$, pD = 9.3.

NMR Titration of 3.0 mM Cytochrome c with 1 in 12 mM $KNO_3$, pD = 9.3.

Micro Calorimetry Titration of 0.10 mM Cytochrome c with 1 in 10 mM $KH_2PO_4$, pH = 8.1. In this plot, heat generated per injection was integrated therefore the y-axis is H not $\Delta H$.

Fluorescence Titration of 0.010 nM Melitten with 1 (open circle) and 2 (closed circle, concentrations of 2 were divided by four upon the plotting to make the residual concentration of loop motif same as that of 1) in 10 mM $KH_2PO_4$, pH = 7.0.
Excitation at 296 nm and emission at 344 nm.

Job's Plot of melittin with 1 in 10 mM KH$_2$PO$_4$, pH = 7.0 at 0.020 mM. Excitation at 296 nm and emission at 344 nm.

5,770,380

SYNTHETIC ANTIBODY MIMICS—MULTIPLE PEPTIDE LOOPS ATTACHED TO A MOLECULAR SCAFFOLD

BACKGROUND OF INVENTION

1. Field of the Invention

The present invention relates to compounds capable of mimicking some of the functions of natural antibodies without having all of their limitations.

2. Brief Description of the Prior Art

Natural antibodies are produced by the immune systems of all animals. In what is called an "immunogenic response," antibodies act to destroy pathogens. The "binding site" of an antibody is used to bind the pathogen to the antibody as an essential early step in the destruction of the pathogen. The immune system is capable of producing millions of different types of antibodies with millions of different binding sites. This diversity of binding sites allows the immune system to respond to each pathogen by producing antibodies specifically tailored to destroy that pathogen.

Natural antibodies are limited in that there is a delay of several days before the immune system recognizes invading pathogens and produces the appropriate antibodies. In addition, antibodies from one animal cannot be made to function with pharmaceutical effectiveness in a second animal. This limitation is caused by two major factors: the large size and the protein character of antibodies. These factors cause the second animal to have an immunogenic response to the non-native antibodies and to begin producing a new set of native antibodies to destroy the non-native antibodies. Yet another limitation of natural antibodies is that their protein character limits their life span in the body due to the presence of protease enzymes in the bloodstream.

Artificially produced antibodies have the same capacity for a diversity of binding sites as natural antibodies. Hybridoma technology allows one to choose from this diversity and produce millions of "monoclonal" antibodies, all of which have exactly the same binding site. Because of this specificity, monoclonal antibodies have many applications, including uses in immunosensors, in diagnostic kits and as catalysts. (Hsieh-Wilson, et al., (1996) Acc. Chem Res. 29:164–170). A limitation of antibodies for such uses, however, is their chemical instability, both in extreme environmental conditions and in the presence of protease enzymes.

Chemicals which mimic the functions of antibodies have also been produced. The advantages of such "antibody mimics" includes their small size, which allows them to avoid provoking an immunogenic response.

There are several approaches to the structure and manufacture of these antibody mimics. One approach utilizes an alternative protein framework, such as cytochrome $b_{562}$. (Hsieh-Wilson, et al., (1996), supra). Limitations of this approach include the vulnerability of protein frameworks to attack by proteases, and their instability to extreme environmental conditions.

Some of the functions of antibodies have been mimicked in structures comprising ribonucleic acids (RNA). The limitations of these structures include the instability and short life span of RNA molecules. (Hsieh-Wilson, et al., (1996), supra).

Unnatural oligomers such as benzodiazepines, beta-turn mimics, protease inhibitors and purine derivatives have also been tested for their ability to function as antibody mimics. Limitations of these oligomers include the limited number of binding sites that can be produced as compared to polymers such as peptides. (Hsieh-Wilson, et al., (1996), supra).

Unnatural biopolymers such as oligocarbamates, oligoureas and oligosulfones have been proposed as antibody mimics. Limitations of these biopolymers are unknown at this time as they are still being tested and developed. (Hsieh-Wilson, et al., (1996), supra).

Molecules with some of the recognition properties of antibodies have been created by joining various substituents to scaffolds such as xanthene and cubane. These substituents include peptides but do not include peptide loops. The limitations of these molecules as antibody mimics include the fact that the substituents that provide the binding properties of the molecule do not all project from the same side of the framework. Thus, the substituents cannot all contact the same antigen at the same time, and therefore binding is reduced. (Hsieh-Wilson, et al., (1996), supra).

Antibody mimics comprising a scaffold of a small molecule such as 3-aminomethylbenzoic acid and a substituent consisting of a single peptide loop have been constructed. The peptide loop performs the binding function in this mimic. The limitations of this mimic include its drastically reduced binding ability due to the presence of only one peptide loop. (Smythe, et al., (1994), J. Am. Chem. Soc. 116:2725–2733)

Thus, although there is a strong interest in other forms of antibody mimics to be used as replacements for natural and monoclonal antibodies, a need still exists for antibody mimics that are stable, that survive under extreme environmental conditions and in the presence of proteases, and that have a great diversity of binding sites and great binding ability.

SUMMARY OF THE INVENTION

The present invention is directed to an antibody mimic which provides multiple peptide loops bound to an organic or molecular scaffold. In a preferred embodiment, the loops all project from the same side of the scaffold with respect to one another. Because of its unique design, said antibody mimic fulfills the above-mentioned needs.

The antibody mimic of the present invention is not large enough to produce an immunogenic response in animals, the way non-native antibodies do. Its scaffold does not consist purely of a peptide, thus it is not as vulnerable to attack by protease enzymes as molecules with peptide scaffolds. Because the scaffold does not consist purely of a peptide, DNA or RNA, it is relatively stable in extreme environmental conditions and has a long life span. Because the binding sites of said antibody mimic are provided by peptide loops, the potential diversity of binding sites is far greater than with other oligomers and polymers. Because the loops project from the same side of the scaffold, all of the loops are available for binding purposes and binding ability is increased.

In a highly preferred embodiment of the invention, the antibody mimic comprises an organic scaffold comprising a calixarene unit to which is linked a plurality of peptide loops.

In another highly preferred embodiment a linking unit is used to link the peptide loops to the scaffold. The calixarene unit may contain two, three, four, five, six, seven, or eight arylcarboxylate groups, although it preferably contains four such groups. Preferably one peptide loop is linked to each arylcarboxylate group.

For the purposes of the present application, the following definitions apply:

"Organic" describes a chemical or group that contains at least one carbon atom.

"Peptide loop" is defined as a chain of amino acids attached at both ends of said chain to an organic or molecular scaffold, either directly, or indirectly through a linking group.

"Same side" describes a geometric relationship between two or more peptide loops directly or indirectly attached to a scaffold wherein at least one imaginary plane passes through said scaffold such that the points of attachment for said loops are all on only one side of said plane.

BRIEF DESCRIPTION OF THE FIGURES

For a fuller understanding of the nature and objects/advantages of the invention, reference should be made to the following detailed description taken in connection with the accompanying drawings forming a part of this specification and in which similar numerals or reference characters indicate corresponding elements depicted illustratively in the drawings:

FIGS. 1A–1D illustrates a preferred synthesis route for a cyclic peptide, in solid phase, useful in practicing the present invention, wherein:

FIG. 1A illustrates the synthesis on an oxime resin precursor;

FIG. 1B illustrates a procedure for checking the substitution level of the oxime resin precursor of FIG. 1A;

FIG. 1C illustrates the synthesis of a preferred spacer, or linking group, useful for linking a cyclic peptide to a scaffold of the present invention; and FIG. 1D illustrates the synthesis of a solid phase cyclic peptide, using the oxime resin precursor of FIG. 1A and the spacer of FIG. 1C.

FIGS. 2A–2C illustrates an alternative synthesis route for a cyclic peptide, in solution phase, also useful in practicing the present invention, wherein:

FIG. 2A illustrates synthesis of a first fragment of the cyclic peptide;

FIG. 2B illustrates synthesis of a second fragment of the cyclic peptide; and

FIG. 2C illustrates synthesis of a cyclic peptide from the first fragment of FIG. 2A and the second fragment of FIG. 2B.

FIG. 3 illustrates a preferred synthesis route for synthesizing a Calix[4]arenetetraacid, useful in practicing the present invention.

FIG. 4 illustrates a preferred synthesis route for synthesizing a calixarene cyclicpeptide of the present invention.

FIG. 5 illustrates a preferred embodiment of the present invention, a synthetic antibody mimic based on a calixarene scaffold.

DETAILED DESCRIPTION OF THE PREFERRED EMBODIMENTS

The present invention relates to a family of synthetic molecules that, like antibodies, have multiple peptide loops as a binding site but, unlike antibodies, contain a rigid, non-peptide, organic scaffold.

The present invention relates to a family of synthetic molecules that, like the antibodies, have multiple peptide loops as the recognition site but built around a rigid organic framework. The design retains a similar structural relationship to the antigen combining region but based on four loops rather than six as occurs in natural antibodies. However, it should be noted that X-ray structures of antibody-antigen complexes show that often only four of the six available loops of natural antibodies make contact to the antigen. See, e.g., Wilson, I. A.; Stanfield, R. L.; Rini, J. M.; Arevalo, J. H.; Schulze-Gahmen, U.; Fremont, D. H.; Stura, E. A.; "Structural Aspects of Antibodies and Antibody-Antigen Complexes" Ciba Foundation Symp. 1991, 159, 13–39. Also, the synthetic route described herein allows the ready generation of large libraries of artificial antibodies that can be screened for binding to target antigens.

The basic design of a preferred antibody mimic of the present invention is shown in FIG. 5. The rigid organic scaffold, generally 10, is provided by a calixarene unit containing four arylcarboxylate groups 12 linked by ortho substitution within a macrocyclic ring. The para-alkyloxy substituent enforces an essentially rigid conformation for the calixarene with all four carboxylate groups projecting onto the same side of the ring, that is, on the same side of an imaginary plane P passing through the ring 10 as illustrated. This conformation is crucial for the design as it allows the close positioning of four peptide loops in direct analogy to the antigen combining site of antibodies.

The peptide loop components are prepared via the route outlined in greater detail herein. A key part of the design is the dipeptide mimetic 3-aminomethylbenzoic acid which allows the formation of a well-defined loop structure corresponding to a type-II β-turn (Bach, A. C.; Eyerman, C. J.; Gross, J. D.; Bower, M. J.; Harlow, R. L.; Weber, P. C.; DeGrado, W. F. "Structural Studies of a Family of High Affinity Ligands for GPIIb/IIIa," J. Am. Chem. Soc. 1994, 116, 3207–3219) but with the potential for attachment to the calixarene scaffold. This is achieved by substitution in the 5-position by a nitro group which is then converted during the synthesis to an amino group for attachment to the calixarene. The synthesis of the cyclic peptides involves either solid phase chemistry or solution phase chemistry using a Kaiser oxime carboxylate activating group, discussed in greater detail subsequently with respect to FIGS. 1–4.

Figure 6:
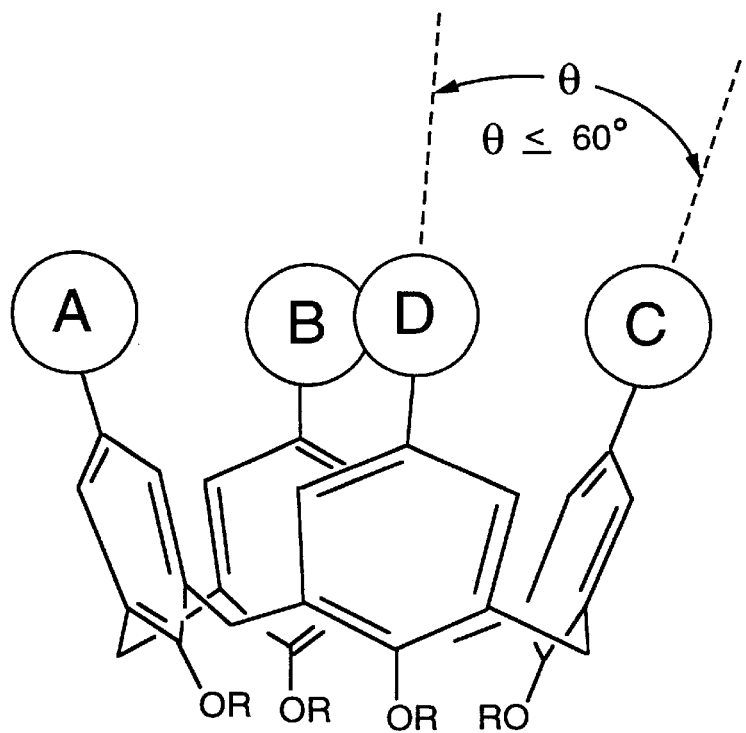
FIG. 6 illustrates another preferred embodiment of the present invention.

Synthesis of the preferred compounds have been carried out on multigram scale of both cyclic peptide and calixarene. Final coupling involves conversion of the calixarene tetraacid to the corresponding tetraacid chloride followed by reaction with the cyclic peptide amine derivative. This strategy allows the user to easily prepare large libraries of antibody mimics based on cyclic peptides with different sequences of four amino acids in the loop. For n different peptide loop structures (A, B, C . . . etc.) as illustrated in FIG. 6, the total number of different combinations (ABCD, ABBD, AADD, . . . etc.) are as follows:

$$\text{Number of total combinations} = \frac{n(n+1)(n^2-n+2)}{4}$$

Thus for 8 different peptide loop structures a total of 1,044 different antibody mimics will be available. This strategy of generating combinatorial libraries of quite different, small organic molecules has previously been reported. By increasing the number of different peptide loops in the synthesis the diversity of artificial combining site structures can increase dramatically.

Figure 7:
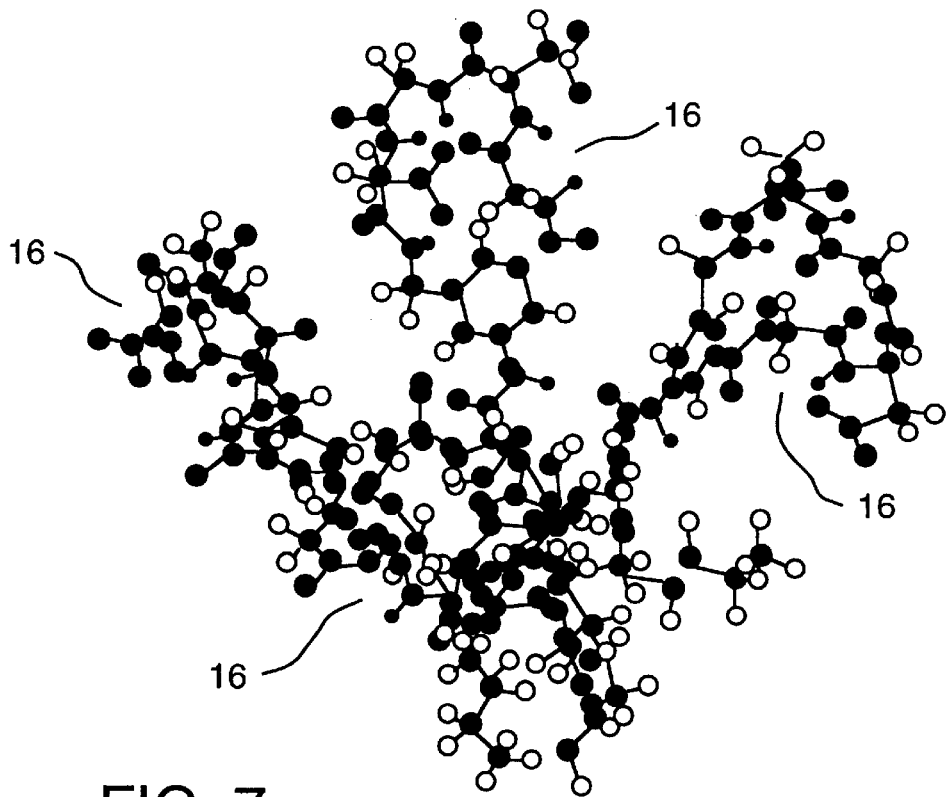
FIG. 7 illustrates a calculated molecular structure for an antibody mimic of the present invention based on a bis-aspartate peptide loop.

FIG. 7 shows a calculated structure for an antibody mimic of the present invention based on the bis-aspartate peptide loop. The structure shows clearly the formation of a well-defined recognition site formed by the four peptide loop components, generally 16. The power of this strategy is that a large number of antibody mimics can be prepared by the synthetic strategy and these can be screened for high affinity binding to a range of different antigen targets. The potential applications are enormous, involving substitution of synthetic antibody mimics into much of the current antibody technology (immunosensors, diagnostic kits, etc.). The increased stability of these compounds should find further application in therapeutics as well as the identification of catalysts that can function under extreme conditions.

Accordingly, a highly preferred method of practicing the present invention involves screening antibody mimics of the present invention for effectiveness as synthetic antibodies capable of binding to target antigens. In accordance with this method, a library consisting of a large number of different antibody mimics is provided, each of the antibody mimics comprising a structure as described herein, preferably an organic scaffold to which is linked a plurality of peptide loops. Each antibody mimic in the library differs from each of the other antibody mimics in the library by having a different combination of peptide loops relative to the other antibody mimics in the library. Once the library of antibody mimics is provided, each of the antibody mimics in the library is capable of being screened for antibody effectiveness relative to other antibody mimics in the library by determining a binding affinity of the particular antibody mimic in the library being screened with respect to a target antigen relative to a binding affinity of one or more other antibody mimics in the library to that same target antigen. Additionally, the library may be used by focusing on a particular antibody mimic and screening that antibody mimic for binding affinity with respect to a number of different target antigens.

Referring again to FIG. 5, in a highly preferred embodiment of the present invention, the scaffold comprises a calixarene ring 10 wherein each of the arene groups 12 that are part of the calixarene ring is linked to a peptide loop X via a linking unit, preferably a 3-aminomethylbenzamide group, generally 14, such as 3-aminomethyl-5-aminobenzamide (see also FIG. 1C) and each of said 3-aminomethylbenzamide groups is linked to the peptide loop, generally 16, where $R_1$ is preferably glycine, $R_2$ is aspartate, $R_3$ is glycine and $R_4$ is aspartate. Of course, other combinations, other linking groups, other organic complexes, and other peptide loop structures are possible as will now be readily apparent to those of ordinary skill in the art. Examples of other possible linking units include 3-aminophenylacetamide and 7-aminonaphthyl-1-carboxamide. Examples of other possible $R_1$, $R_2$, $R_3$, and $R_4$ groups, which may be the same or different, include lysine, arginine, histidine, phenylalanine, serine, alanine, leucine, tyrosine, tryptophen, and glutamic acid.

In addition to calixarenes, the molecular scaffold of the present invention may comprise synthetic proteins, porphyrins, tetra arylcyclophanes, and metal-ligand complexes.

It is understood in the art that the number "3" in "3-aminomethylbenzamide" (hereinafter Mamb) refers to the position of the carbon atom in the aryl portion of the Mamb group that is connected to the carbon of the methyl part of the aminomethyl portion of the Mamb group. It is also understood in the art that the number 1 position of the Mamb group is at the carbon atom in the aryl portion of the Mamb group that is connected to the amide portion of the Mamb group.

For the purposes of this specification, the numbering is of the arene groups that form the calixarene scaffold begins with 1 at the position of attachment to each Mamb linking group. As shown in FIG. 5, all of the 3 and 5 positions of said arene groups are linked, respectively, to the 5 and 3 positions of adjacent arene groups in order to form the calixarene ring. The 4 position of each arene ring is linked to an alkyloxy group, where R is preferably n-butyl, but may also be n-propyl, benzyl, 2-napthylmethyl or other groups, including fluoresent groups for use in detecting substrate binding.

In the preferred embodiment of the present invention, a peptide loop rather than an open-ended peptide chain is preferred because such loops are more chemically stable than open-ended chains. In addition, such loops more closely mimic the loop structures of the binding sites of antibodies.

In the preferred embodiment of the present invention, Mamb is used as a linking group because, as a dipeptide mimetic, two points on Mamb can be made to attach to the two ends of the peptide chain. The manner of this attachment resembles a type-II beta-turn, which allows the formation of a well-defined peptide loop structure, and mimics the beta-turn structures that exist in four out of the six hypervariable loops of natural antibodies. In addition, a third point on the Mamb group can be made to attach to the calixarene scaffold. Thus, Mamb not only becomes a part of a peptide loop structure, but it also links the loop structure to the scaffold structure. The procedure for attaching Mamb in this three-fold manner is described in greater detail subsequently.

In the preferred embodiment of the present invention, a calixarene scaffold is used because its ring structure and non-protein nature give it stability in extreme environmental conditions and in the presence of protease enzymes. In addition, its ring structure, as detailed below, helps force the attached peptide loops to come into close proximity to each other, mimicking the binding site of an antibody. Finally, the arene groups of the calixarene rings may be attached at their number four positions to alkyloxy groups.

The above-mentioned alkyloxy groups are important in the preferred embodiment of the present invention because they enforce the rigid three-dimensional conformation of the calixarene scaffold. In two dimensions, calixarene is a ring, however, in three dimensions the ring is seen to have a cup-like conformation, as is illustrated in FIGS. 5 and 6. The side of the cup from which the alkyloxy groups project, that is, the "4" positions of the arene groups, may be called the bottom of the cup. Thus the opposite side, which is the side attached to the peptide loops, that is, the "1" positions of the arene groups, may be called the top of the cup. Because the alkyloxy groups (OR) attached to the bottom of the cup reenforce the cup conformation, all of the peptide loops X at the top of the cup are forced into close proximity to one another. This close proximity of the peptide loops, in turn, mimics the structure of an antibody and forces all of the peptide loops to be available for contact with and binding to an antigen of interest. As illustrated, the peptide loops X all project from the same side of the scaffold 10, i.e., all points of attachment, 1, of the loops X, lie on the same side of imaginary plane P passing through the scaffold 10.

A highly preferred embodiment of the present invention uses between four and eight peptide loops to form the binding site of the antibody mimic. This embodiment is highly preferred because in many natural antibodies, only four of the six hypervariable loops of the antibody actually participate in binding to the antibody's antigen. (Wilson, et al., (1991) Ciba Foundation Symp., 159:13–39). Thus it is possible to duplicate the binding strength of many antibodies by using just four peptide loops in an antibody mimic. More loops may be added to increase or change the binding characteristics of an antibody mimic, however, if more than eight loops are used, the distance between loops may weaken the ability of an antibody mimic to bind a target molecule.

A more highly preferred embodiment of the present invention uses four peptide loops to form the binding site of the antibody mimic. The four peptide loops are connected to four different Mamb linking groups. These four Mamb linking groups, in turn, are linked to the four arylcarboxamide groups of a calix[4]arene scaffold at the "1" position of each aryl portion of each arylcarboxamide group. Finally, each aryl portion of each arylcarboxamide group is connected at its "4" position to an alkyloxy group selected from the group consisting of n-butyl, n-propyl, benzyl, 2-naphthylmethyl or other fluorescent groups to assist in detecting substrate binding.

The above embodiment is more highly preferred because the synthesis of calix[4]arene is simpler than calixarene molecules with more than four arene groups in the calixarene ring. Said embodiment is also conformationally stable, an aid in its ability to bind tightly to target molecules. Finally, as discussed supra, in many cases, only four loops are required to bind target molecules.

A most highly preferred embodiment of the present invention has four peptide loops X as illustrated in FIG. 5. In this embodiment, each of the four loops X has an identical structure. As FIG. 5 shows, amino acid residue is a glycine residue wherein the nitrogen of the amino end of the glycine residue is also the nitrogen that comprises the amide end of the Mamb linking group. Additionally, in this embodiment amino acid residue is an aspartate residue and amino acid residue is a glycine residue. The final residue of each loop is an aspartate residue wherein the carboxyl end of the residue is connected to the nitrogen of the aminomethyl portion of the Mamb linking group. In this highly preferred embodiment of the present invention, the alkyloxy groups are identical and consist of n-butyl groups. This embodiment is highly preferred because experimental evidence has shown that it binds tightly to its target molecule, cytochrome C. Many other sequences, however, for use with other target molecules are, of course, possible, and are within the scope of the present invention.

I. Synthesis of Cyclic Peptide in Solid Phase

A. Synthesis of Oxime Resin

Referring to FIG. 1A, the synthesis scheme for synthesizing an oxime resin, useful as a precursor in the solid phase preparation of a cyclic peptide is illustrated, wherein polystyrene resin and p-nitrobenzoyl chloride are reacted with the other reactants illustrated, to yield the oxime resin, 20. Certain particulars of the synthesis are as follows:

p-Nitrobenzoyl resin (HMY2501). p-Nitrobenzoyl chloride (27.84 g, 150 mmol) and alminium chloride (28.04 g, 213 mmol) were dissolved in dry $CH_2Cl_2$ (700 mL). Bio-Beads SX-1 (100 g) was added to the reaction mixture and stirred at room temperature for two hour. The reaction mixture was collected on a Buchner funnel and washed with 1/3=4N HCl/dioxane (2 L), 1/3=water/dioxane (2 L), DMF (2 L), MeOH (2 L), $CH_2Cl_2$ (2 L) and MeOH (2 L). The resin was dried under vacuum to give pale yellow powder (119.6 g).

Oxime resin (HMY2503). A suspension of hydroxylamine hydrochloride (41.2 g, 593 mmol), ketoresin (30 g) and pyridine (40 mL) in EtOH (200 mL) was heated to gentle reflux for 12 hours. The resin was collected on a glass filter and washed with MeOH (4×50 mL). The residue was dried under vacuum to give pale yellow powder (30.7 g). For more information concerning synthesis of oxime resin, see, Scarr, R. B.; Findeis, M. A. *Peptide Research* 1990, 3, 238–241, incorporated in its entirety by reference herein.

B. Checking the Substitution Level

It is important to check the substitution level of the oxime resin in order to determine the necessary stoichiometry of the reacting amino acid. This checking is accomplished according to the procedures outlined in Stewart, J. M.; Young, J. D. *Solid Phase Peptide Synthesis;* 2nd ed.; Pierce Chemical Co.: Rockford, Ill., 1984, pp 107–108, incorporated in its entirety by reference herein. The general procedure, illustrated in FIG. 1B, was as follows:

Aminoacylation (HMY2504). A suspension of oxime resin (350 mg), Boc-Gly-OH (111 mg, 0.63 mmol) and DCC (136 mg, 0.66 mmol) in dry $CH_2Cl_2$ (4 mL) was shaken overnight. The solution was drained off from a glass filter and washed with $CH_2Cl_2$ (2×16 mL), DMF (2×16 mL), $CH_2Cl_2$ (2×16 mL) and MeOH (16 mL). Boc Deprotection (HMY2505). A suspension of aminoacylated resin and TFA (1.5 mL) in $CH_2Cl_2$ (4.5 mL) was shaken for 30 minutes. The solution was drained off from a glass filter and washed with CH2Cl2 (4×10 mL), i-PrOH (10 mL), $CH_2Cl_2$ (2×10 mL), i-PrOH (10 mL) and $CH_2Cl_2$ (4×10 mL). Picric Acid Titration (HMY2506). <Reagent A> Picric acid (10% water, 2520 mg, 9.90 mmol) was dissolved in water (100 mL). <Reagent B> DIEA (5 mL) was dissolved in $CH_2Cl_2$ (95 mL). Deprotected resin was added $CH_2Cl_2$ to swell and then washed with Reagent B (2×10 mL) to neutralize, $CH_2Cl_2$ (5×10 mL) to remove excess base, Reagent A (2×10 mL) to form picrate salt, $CH_2Cl_2$ (5×10 mL) to remove excess acid and finally washed with Reagent B (2×10 mL) and collected all of washings. The final washings was diluted to 100 mL with EtOH. 1 mL of the EtOH solution was diluted to 100 mL with EtOH. The absorbance of diluted solution at 358 nm in 10 mm cell was 2.74. The extinct coefficient of DIEA picrate at 358 nm is 14500, therefore the substitution level of the resin was calculated to be 0.54 mmol/g.

C. Synthesis of Cyclic Peptide by Solid Phase Peptide Synthesis

FIG. 1D illustrates a preferred synthesis scheme for preparing a cyclic peptide in solid phase. The spacer, or linking unit, 14, illustrated in FIG. 1C used in the peptide loop, may be synthesized as follows:

3-Methoxycabonyl-5-nitrobenzamide (HMY2139). A solution of mono-methyl 5-nitroisophthalate (45.0 g, 200 mmol), thionyl chloride (71.4 g, 600 mmol) and DMF through $SiO_2$ (125 μL) in dry THF (100 mL) and dry $CH_2Cl_2$ (300 mL) was refluxed overnight. See, FIG. 1C, step 1. The reaction mixture was evaporated in vacuo and then added dry $CH_2Cl_2$ (200 mL) and hexanes (500 mL). Ammonia gas was introduced into the solution and the precipitation was collected on a glass-filter. Id., step 2. The cake was suspended in 1N HCl (500 mL), filtered again and then washed with saturated NaHCO₃ aq. (500 mL) and water (500 mL). The product was dried in vacuo to give ivory powder (36.3 g, 81%): $^1$H NMR (300 MHz, DMSO-$d_6$) δ 8.918 (t, J=1.8 Hz, 1H), 8.816 (t, J=1.2 Hz, 1H), 8.773 (t, J=1.6 Hz, 1H), 8.716 (s, 1H, NH), 7.859 (s, 1H, NH), 3.944 (s, 3H); $^{13}$C NMR (300 MHz, DMSO-$d_6$) δ 164.9, 164.2, 148.1, 136.4, 134.9, 133.8, 133.3, 131.5, 126.4, 126.0, 53.1.

Methyl 3-nitro-5-aminomethybenzoate (HMY2220). A mixture of 3-methoxycabonyl-5-nitrobenzamide (1120 mg, 5 mmol) and 1M BH₃ in THF (11.5 mL) was refluxed for 90 minutes. For a detailed description of techniques for borane reduction, see Brown, H. C.; Heim, P. *J. Org. Chem. 1973, 38*, 912–916. The solvent was evaporated and MeOH (15 mL) was added. HCl gas was introduced into the solution and the reaction mixture was refluxed for 70 minutes. The mixture was added saturated NaHCO₃ aq. (50 mL) and extracted with CH₂Cl₂ (5×40 mL). The organic layers were combined, washed with brine and dried over Na₂SO₄. The dried solution was applied directly to SiO₂ column and developed with AcOEt then 1/10=MeOH/AcOEt. The elution was evaporated to give the desired product (361 mg, 34%): $^1$H NMR (300 MHz, CDCl₃) δ 8.696 (s, 1H), 8.403 (s, 1H), 8.320 (s, 1H), 4.051 (s, 2H), 3.961 (s, 3H); $^{13}$C NMR (300 MHz, CDCl₃) δ 165.0, 148.3, 145.9, 133.7, 131.7, 125.8, 122.8, 52.7, 45.2; HRMS m/e calc'd for $C_9H_{10}N_2O_4$: 209.0562, found 209.0565.

3-tert-Butoxycarbonylaminomethyl-5-nitrobenzoic acid (HMY2618). A solution of methyl 5-nitro-3-aminomethybenzoate (1980 mg, 9.4 mmol) in 1N NaOH (28 mL, 28 mmol) and tert-BuOH (20 mL) was stirred at r.t. for 10 hours and then added BOC₂O (4100 mg, 18.8 mmol) and stirred for 17 hours. The reaction mixture was added hexanes (50 mL) and water (50 mL). The aqueous layer was acidified with 5% citric acid aq. and extracted with CH₂Cl₂ (2×70 mL). The CH₂Cl₂ layers were combined and washed with water (50 mL). The organic layer was evaporated to give the desired compound (2450 mg, 88%): $^1$H NMR (300 MHz, DMSO-$d_6$) δ 13.725 (s, 1H), 8.476 (s, 1H), 8.307 (s, 1H), 8.216 (s, 1H), 7.639 (t, J=5.7 Hz, 1H), 4.398 (d, J=5.7 Hz, 2H), 1.385 (s, 9H); $^{13}$C NMR (300 MHz, DMSO-$d_6$) δ 165.5, 155.9, 147.9, 143.5, 133.6, 132.5, 125.4, 122.2, 78.3, 42.6, 28.2.

cyclo-(Gly-Asp(OcHx)-Gly-Asp(OcHx)-3Am5nb) (HMY2520). Solid phase peptide synthesis was carried out following the procedure in: Jackson, S.; DeGrado, W.; Dwivedi, A.; Parthasarathy, A.; Higley, A.; Krywko, J.; Rockwell, A.; Markwalder, J.; Wells, G.; Wexler, R.; Mousa, S.; Harlow, R., *J. Am. Chem. Soc.* 1994, 116, 3220–3230, incorporated in its entirety by reference herein. <First Coupling> A suspension of 3-Boc-aminomethyl-5-nitrobenzoic acid (498 mg, 1.68 mmol), DCC (347 mg, 1.68 mmol), DMAP (205 mg, 1.68 mmol) and oxime resin (2000 mg, 1.08 mmol) in dry CH₂Cl₂ (20 mL) was placed in solid phase peptide synthesis apparatus and shaken at r.t. overnight. The solution was removed by suction and the residue was washed with DMF (3×15 mL), MeOH (15 mL), CH₂Cl₂ (3×15 mL), MeOH (15 mL) and CH₂Cl₂ (3×15 mL). The residue was dried in vacuo.

<Checking the Coupling Level> A 100 mg of the residue was sampled, added CH₂Cl₂ (1 mL) and TFA (0.3 mL) and stirred at r.t. for one hour. The solution was removed by suction and the resin was swelled with trace amount of CH₂Cl₂. The resin was neutralized with 5% DIEA in CH₂Cl₂ (2×10 mL) and then washed with CH₂Cl₂ (5×10 mL). The neutral resin was added 0.1M picric acid in CH₂Cl₂ (2×10 mL) to make its salt and the excess picric acid was washed away with CH₂Cl₂ (5×10 mL). The salt was washed with 5% DIEA in CH₂Cl₂ (2×10 mL) and the washings were collected and diluted to 100 mL with EtOH. A 1 mL of the EtOH solution was diluted to 10 mL and the UV was measured to know the concentration. The absorbance at 358 nm was 0.640 in 10 mm cell and the extinct coefficient of DIEA picrate was 14500, therefore the resin's coupling level was 0.44 mmol/g.

<Blocking the Resin> A mixture of the resin, trimethylacetyl chloride (603 mg, 5 mmol) and DIEA (646 mg, 5 mmol) in DMF (10 mL) was shaken at r.t. overnight. The solution was removed by suction and washed with DMF (3×20 mL), MeOH (20 mL), CH₂Cl₂ (3×20 mL), MeOH (2×20 mL) and CH₂Cl₂ (3×20 mL).

<Deprotection of tert-Boc group> The resin was shaken in 25% TFA/75% CH₂Cl₂ solution (20 mL) at r.t. for one hour. The solution was removed by suction and the resin was washed with CH₂Cl₂ (3×20 mL), MeOH (20 mL) and CH₂Cl₂ (3×20 mL). The residue was dried in vacuo.

<Coupling> Boc-Asp(OcHx)-OH (2120 mg, 6.72 mmol) and BOP (2970 mg, 6.72 mmol) and HOBt (955 mg, 6.72 mmol), DMF (20 mL) and NMM (2.22 mL, 20.2 mmol) were added to the resin and the mixture was shaken at r.t. overnight. Then the solution was removed by suction and the resin was washed with DMF (20 mL), MeOH (20 mL), CH₂Cl₂ (3×20 mL), MeOH (2×20 mL) and CH₂Cl₂ (3×20 mL). The resin was dried in vacuo.

<Repetition> The deprotection and the coupling were repeated three more times with appropriate Boc amino acids.

<Deprotection and Neutralization> The resin was shaken in 25% TFA/75% CH₂Cl₂ solution (20 mL) at r.t. for one hour. The solution was removed by suction and the resin was washed with CH₂Cl₂ (3×20 mL), MeOH (20 mL) and CH₂Cl₂ (3×20 mL), then neutralized by washing with 10% DIEA in CH₂Cl₂ (2×20 mL), CH₂Cl₂ (3×20 mL), MeOH (3×20 mL). The resin was dried in vacuo.

<Cyclization> The resin was added DMF (100 mL) and AcOH (96 mL) and the mixture was warmed up 50° C. for 72 hours. The resin was filtered off and washed with DMF. The filtrate was evaporated, added water (100 mL) to solidify the product and dried in vacuo. The crude product was purified by preparative TLC (SiO₂, 1/10=MeOH/CH₂Cl₂) to give the cyclic peptide (134 mg, 17% from resin): $^1$H NMR (300 MHz, DMSO-$d_6$) δ 9.516 (t, J=5.1 Hz, 1H), 8.792 (t, J=6.0 Hz, 1H), 8.483 (s, 1H), 8.323 (s, 1H), 8.304 (d, J=8.1 Hz, 1H), 8.044 (d, J=8.4 Hz, 1H), 8.004 (s, 1H), 7.829 (t, J=5.7 Hz, 1H), 4.8–4.6 (m, 5H), 4.090 (dd, J=4.5, 16.8 Hz, 1H), 3.9–3.6 (m, 4H), 2.825 (dd, J=5.4, 15.6 Hz, 1H), 2.646 (dd, J=5.4, 16.2 Hz, 1H), 2.5–2.3 (m, 2H), 1.636 (m, 8H), 1.279 (m, 12H); LRMS (FAB) m/e calc'd for $C_{32}H_{43}N_6O_{11}$ (M+H$^+$): 687.299, found 687.355.

cyclo-(Gly-Asp(OcHx)-Gly-Asp(OcHx)-3Am5ab) (HMY2521). A solution of the cyclic peptide (130 mg, 0.19 mmol) and 10% Pd/C (120 mg) in dry THF (10 mL) was added water (3 mL) and placed in 100-mL round bottom flask. Hydrogen was introduced after removal of air by an aspirator and the solution was stirred vigorously overnight. The catalyst was removed by filtration with celite. The filtrate was evaporated in vacuo to give the desired compound (124 mg, 100%): $^1$H NMR (300 MHz, methanol-$d_4$) δ 6.945 (s, 1H), 6.888 (s, 1H), 6.702 (s, 1H), 4.8–4.6 (m, 5H), 4.2–3.8 (m, 5H), 3.0–2.5 (m, 4H), 1.757 (m, 8H), 1.409 (m, 12H).

II. Synthesis of Cyclic Peptide in Solution Phase

FIG. 2 illustrates a preferred synthesis scheme for synthesizing cyclic peptides in solution phase, discussed in detail below. For more details concerning peptide synthesis in solution phase, see Bodanszky, M.; Bodanszky, A. *The Practice of Peptide Synthesis;* 2nd ed.; Springer-Verlag: 1994, incorporated in its entirety by reference herein.

3-Methoxycabonyl-5-nitrobenzamide (HMY2139). A solution of mono-methyl 5-nitroisophthalate (45.0 g, 200 mmol), thionyl chloride (71.4 g, 600 mmol) and DMF through $SiO_2$ (125 µL) in dry THF (100 mL) and dry $CH_2Cl_2$ (300 mL) was refluxed overnight. The reaction mixture was evaporated in vacuo and then added dry $CH_2Cl_2$ (200 mL) and hexanes (500 mL). Ammonia gas was introduced into the solution and the precipitation was collected on a glass-filter. The cake was suspended in 1N HCl (500 mL), filtered again and then washed with saturated NaHCO3 aq. (500 mL) and water (500 mL). The product was dried in vacuo to give ivory powder (36.3 g, 81%): $^1$H NMR (300 MHz, DMSO-$d_6$) δ 8.918 (t, J=1.8 Hz, 1H), 8.816 (t, J=1.2 Hz, 1H), 8.773 (t, J=1.6 Hz, 1H), 8.716 (s, 1H, NH), 7.859 (s, 1H, NH), 3.944 (s, 3H); $^{13}$C NMR (300 MHz, DMSO-$d_6$) δ 164.9, 164.2, 148.1, 136.4, 134.9, 133.8, 133.3, 131.5, 126.4, 126.0, 53.1.

Methy 3-aminomethyl-5-nitrobenzoate (HMY2220). A mixture of 3-methoxycabonyl-5-nitrobenzamide (1120 mg, 5 mmol) and 1M $BH_3$ in THF (11.5 mL) was refluxed for 90 minutes. The solvent was evaporated and MeOH (15 mL) was added. HCl gas was introduced into the solution and the reaction mixture was refluxed for 70 minutes. The mixture was added saturated $NaHCO_3$ aq. (50 mL) and extracted with $CH_2Cl_2$ (5×40 mL). The organic layers were combined, washed with brine and dried over $Na_2SO_4$. The dried solution was applied directly to $SiO_2$ column and developed with AcOEt then 1/10=MeOH/AcOEt. The elution was evaporated to give the desired product (361 mg, 34%): $^1$H NMR (300 MHz, CDCl$_3$) δ 8.696 (s, 1H), 8.403 (s, 1H), 8.320 (s, 1H), 4.051 (s, 2H), 3.961 (s, 3H); $^{13}$C NMR (300 MHz, CDCl$_3$) δ 165.0, 148.3, 145.9, 133.7, 131.7, 125.8, 122.8, 52.7, 45.2; HRMS m/e calc'd for $C_9H_{10}N_2O_4$: 209.0562, found 209.0565.

3-Aminomethyl-5-nitrobenzoic acid (HMY2717). To a solution of methyl 3-aminomethyl-5-nitrobenzoate (5890 mg, 28 mmol) in THF (100 mL) was added a solution of LiOH (2350 mg, 56 mmol) in water (100 mL) and the mixture was stirred at r.t. for 2.5 hours. THF was evaporated and the aqueous solution was washed with $Et_2O$ (100 mL). The solution was neutralized with concentrated HCl (6 mL) and evaporated in vacuo. To a solution of evaporated residue in water (150 mL) and concentrated HCl (3 mL) was added 1N LiOH (50 mL). Brown fine needles were precipitated out and collected on a glass filter (5300 mg, 96%): $^1$H NMR (300 MHz, $D_2O$) δ 8.645 (s, 1H), 8.412 (s, 1H), 8.232 (s, 1H), 4.332 (s, 2H).

Fmoc-Asp(OBut)-3Am5nb-OR (HMY2739). A mixture of Fmoc-Asp(OBut)-OH (3750 mg, 9.1 mmol), SuOH (1050 mg, 9.1 mmol) and DCC (1880 mg, 9.1 mmol) in dry THF (30 mL) was placed in refrigerator at 5° C. for six hours. The precipitated urea was filtered off and the filtrate was evaporated. The evaporated residue was triturated from hexanes and the N-hydroxysuccinimide ester was dried in vacuo (5090 mg, 110%). To a solution of 3-aminomethyl-5-nitrobenzoic acid (1750 mg, 8.9 mmol) and $NaHCO_3$ (1500 mg, 17.8 mmol) in water (45 mL) was added a solution of Fmoc-Asp(OBut)-OSu (91% pure, 3980 mg, 7.1 mmol) in THF (45 mL) and the mixture was stirred at r.t. for 18 hours. The mixture was added $CH_2Cl_2$ (300 mL) and washed with 1N HCl (200 mL) and water (200 mL). The organic layer was evaporated and then recrystallized from EtOH (90 mL) and water (90 mL) to give the titled compound (4000 mg, 95%): $^1$H NMR (300 MHz, DMSO-$d_6$) δ 13.653 (s, 1H), 8.689 (t, J=6.0 Hz, 1H), 8.471 (s, 1H), 8.343 (s, 1H), 8.247 (s, 1H), 7.873 (d, J=7.5 Hz, 2H), 7.8–7.5 (m, 3H), 7.397 (t, J=7.4 Hz, 2H), 7.95 (t, J=7.4 Hz, 2H), 4.5–4.1 (m, 6H), 2.693 (dd, J=15.9, 5.7 Hz, 1H), 2.486 (dd, J=15.9, 5.7 Hz, 1H), 1.330 (s, 9H); $^{13}$C NMR (300 MHz, DMSO-$d_6$) δ 170.9, 169.3, 165.5, 155.8, 147.9, 143.8, 142.7, 140.7, 134.2, 132.4, 127.6, 127.0, 125.8, 125.3, 122.2, 120.1, 80.2, 65.8, 51.5, 46.6, 41.6, 37.4, 27.6.

Cbz-Asp(OBut)-Gly-OBn (HMY2715). A mixture of Cbz-Asp(OBut)-OH (3590 mg, 11.1 mmol), HCl+H-Gly-OBn (3360 mg, 16.6 mmol), EDCI (3180 mg, 16.6 mmol), HOBt (2250 mg, 16.6 mmol) and DIEA (2900 mg, 16.6 mmol) in dry $CH_2Cl_2$ (50 mL) was stirred at r.t. for six hours. The reaction mixture was added $CH_2Cl_2$ (150 mL) and washed with 1N HCl (200 mL), saturated $NaHCO_3$ aq. (200 mL) and brine (200 mL). The organic layer was passed through an inch of $SiO_2$ layer and the $SiO_2$ was washed with 1/9=AcOEt/$CH_2Cl_2$ (200 mL). The eluent was evaporated in vacuo to give clear oil (5690 mg, 100%): $^1$H NMR (300 MHz, CDCl$_3$) δ 7.368 (s, 10H), 7.082 (t, 1H), 6.013 (d, J=7.8 Hz, 1H), 5.164 (s, 2H), 5.126 (s, 2H), 4.592 (d, J=6.6 Hz, 1H), 4.072 (d, J=5.7 Hz, 2H), 2.891 (dd, J=18.2, 4.5 Hz, 1H), 2.641 (dd, J=17.1, 6.3 Hz, 1H), 1.423 (s, 9H); $^{13}$C NMR (300 MHz, CDCl$_3$) δ 171.0, 170.9, 169.3, 136.1, 135.2, 129.7, 128.6 (2C), 128.4, 128.3, 128.2, 81.9, 67.3, 67.2, 51.1, 41.5, 37.3, 28.0.

H-Asp(OBut)-Gly-OH (HMY2724). A solution of the Cbz-Asp(OBut)-Gly-OBn (5090 mg, 9.9 mmol) and 10% Pd/C (400 mg) in MeOH (50 mL) was prepared in a hydrogenator. Hydrogen (43 psi) was introduced after removal of air by an aspirator and the mixture was shaken for four hours. The catalyst was removed by filtration with celite. The filtrate was evaporated in vacuo to give the desired compound (2730 mg, 100%): $^1$H NMR (300 MHz, DMSO-$d_6$) δ 8.585 (t, J=8.8 Hz, 1H), 7.909 (broad s, 3H), 3.905 (t, J=6.2 Hz, 1H), 3.752 (m, 2H), 2.742 (dd, J=15.8, 5.1 Hz, 1H), 2.644 (dd, J=17.0, 7.1 Hz, 1H), 1.395 (s, 9H).

Cbz-Gly-Asp(OBut)-Gly-OH (HMY2731). A mixture of Cbz-Gly-OH (6280 mg, 30 mmol), SuOH (3450 mg, 30 mmol) and DCC (6190 mg, 30 mmol) in dry THF (50 mL) was place d in refrigerator at 5° C. for 11 hours. The precipitated urea was filtered off and the filtrate was evaporated. The evaporated residue was triturated from CHCl3/hexanes and the N-hydroxysuccinimide ester was dried in vacuo (8140 mg, 89%). To a solution of H-Asp(OBut)-Gly-OH (2020 mg, 8.2 mmol) and $NaHCO_3$ (1380 mg, 16.4 mmol) in water (40 mL) was added a solution of Cbz-Gly-OSu (2520 mg, 8.2 mmol) in THF (40 mL) and the mixture was stirred at r.t. for two hours. The mixture was added $CH_2Cl_2$ (200 mL) and washed with 1N HCl (200 mL) and water (200 mL). The organic layer was evaporated to give the titled compound (3330 mg, 93%): $^1$H NMR (300 MHz, DMSO-$d_6$) δ 12.552 (s, 1H), 8.169 (m, 2H), 7.450 (t, J=6.0 Hz, 1H), 7.386 (s, 5H), 5.018 (s, 2H), 4.650 (qd, J=7.3, 2.4 Hz, 1H), 3.8–3.5 (m, 4H), 2.641 (dd, J=15.9, 5.4 Hz, 1H), 2.424 (dd, J=15.9, 8.1 Hz, 1H), 1.363 (s, 9H); $^{13}$C NMR (300 MHz, DMSO-$d_6$) δ 171.0, 170.7, 169.2, 169.0, 156.5, 137.0, 128.4, 127.8 (2C), 80.2, 65.5, 49.2, 43.5, 40.8, 37.7, 27.7.

H-Gly-Asp(OBut)-Gly-OH (HMY2733). A solution of the Cbz-Gly-Asp(OBut)-Gly-OBn (3720 mg, 8.5 mmol) and 10% Pd/C (375 mg) in MeOH (100 mL) was prepared in a hydrogenator. Hydrogen (44 psi) was introduced after removal of air by an aspirator and the mixture was shaken for two hours. Water (100 mL) was added to dissolve precipitation and then the catalyst was removed by filtration with celite. The filtrate was evaporated in vacuo to give the desired compound (2780 mg, 92%): $^1$H NMR (300 MHz, D$_2$O) δ 3.9–3.6 (m, 4H), 2.857 (dd, J=16.5, 5.4 Hz, 1H), 2.715 (dd, J=16.5, 7.8 Hz, 1H), 1.400 (s, 9H).

Fmoc-Asp(OBut)-3Am5nb-Gly-Asp(OBut)-Gly-OH (HMY2749). A mixture of Fmoc-Asp(OBut)-3Am5nb-OH (3950 mg, 6.7 mmol), SuOH (770 mg, 6.7 mmol) and DCC (1380 mg, 6.7 mmol) in dry THF (30 mL) was place d in refrigerator at 5° C. for 17 hours. The precipitated urea was filtered off and the filtrate was evaporated. The evaporated residue was triturated from hexanes and the N-hydroxysuccinimide ester was dried in vacuo (5040 mg, 110%). To a solution of H-Gly-Asp(OBut)-Gly-OH (2030 mg, 6.7 mmol) and NaHCO$_3$ (563 mg, 13.4 mmol) in water (30 mL) was added a solution of Fmoc-Asp(OBut)-3Am5nb-OSu (91% pure, 5040 mg, 6.7 mmol) in THF (30 mL) and the mixture was stirred at r.t. for 11 hours. The mixture was added AcOEt (200 mL) and washed with 1N HCl (200 mL) and brine (200 mL). The organic layer was dried over Na$_2$SO$_4$, evaporated and then triturated from AcOEt/hexanes to give the titled compound as white powder (4770 mg, 81%): $^1$H NMR (300 MHz, DMSO-d$_6$) δ 9.215 (t, 1H), 8.804 (t, J=5.6 Hz, 1H), 8.591 (s, 1H), 8.411 (d, J=8.1 Hz, 1H), 8.272 (s, 2H), 8.0–7.6 (m, 5), 7.395 (t, J=7.4 Hz, 2H), 7.293 (t, J=7.4 Hz, 2H), 4.671 (d, J=6.0 Hz, 1H), 4.5–4.1 (m, 7H), 4.012 (broad s, 2H), 3.622 (broad s, 2H), 2.707 (dd, J=15.9, 5.7 Hz, 2H), 2.490 (m, 2H), 1.352 (s, 9H), 1.335 (s, 9H); $^{13}$C NMR (300 MHz, DMSO-d$_6$) δ 170.9, 170.3, 169.3, 168.6, 164.5, 155.8, 147.8, 143.8, 143.7, 142.3, 140.7, 135.4, 132.9, 127.6, 127.0, 125.3, 124.4, 120.6, 120.1, 80.1, 65.8, 51.6, 49.4, 46.6, 42.8, 41.7, 37.5, 27.6.

cyclo-(Gly-Asp(OBut)-Gly-Asp(OBut)-3Am5nb) (HMY2806). Cyclization condition was taken from: Xue, C.-B.; DeGrado, W. F. *J. Org. Chem.*, 1995, 60, 946–952, incorporated in its entirety by reference herein. A solution of Fmoc-Asp(OBut)-3Am5nb-Gly-Asp(OBut)-Gly-OH (4680 mg, 5.34 mmol) and DMAP (3920 mg, 32.1 mmol) in DMF (100 mL) was stirred for 15 hours at room temperature. This solution was then added to a solution of TBTU (1720 mg, 5.34 mmol) in DMF (100 mL) dropwise for three hours and the mixture was stirred additional one hour. The mixture was added AcOEt (1000 mL) and washed with 1N HCl (2×500 mL) and saturated NaHCO$_3$ (2×500 mL). The crude product was purified by chromatography (SiO$_2$, AcOEt and then 1/10=MeOH/AcOEt) and trituration from AcOEt and hexanes to give desired compound as yellow powder (2360 mg, 70%): $^1$H NMR (300 MHz, DMSO-d$_6$) δ 9.557 (t, J=5.1 Hz, 1H), 8.792 (t, J=6.0 Hz, 1H), 8.520 (s, 1H), 8.359 (s, 1H), 8.310 (d, J=9.3 Hz, 1H), 8.052 (s, 1H), 8.039 (d, J=8.4 Hz, 1H), 7.838 (t, J=5.7 Hz, 1H), 4.8–4.7 (m, 3H), 4.135 (dd, J=16.8, 4.5 Hz, 1H), 4.0–3.7 (m, 4H), 2.825 (dd, J=15.6, 5.4 Hz, 1H), 2.646 (dd, J=15.6, 8.4 Hz, 1H), 2.5–2.3 (m, 2H), 1.369 (m, 9H), 1.361 (m, 9H); $^{13}$C NMR (300 MHz, DMSO-d$_6$) δ 170.4 (2C), 169.7, 169.11, 168.7, 168.2, 166.7, 147.3, 142.7, 135.1, 124.5, 119.8, 80.2, 80.1, 49.1, 44.5, 42.2, 41.0, 37.4, 36.7, 27.6 (2C); LRMS (FAB) m/e calc'd for C$_{28}$H$_{39}$N$_6$O$_{11}$ (M+H$^+$): 635.2677, found 635.5.

cyclo-(Gly-Asp(OBut)-Gly-Asp(OBut)-3Am5ab) (HMY2843). A solution of the cyclic peptide (2290 mg, 3.6 mmol) and 10% Pd/C (400 mg) in MeOH (50 mL) was added water (3 mL) and placed in 250-mL round bottom flask. Hydrogen was introduced after removal of air by an aspirator and the mixture was stirred vigorously for seven hours. The catalyst was removed by filtration with celite. The filtrate was evaporated in vacuo. The crude product was purified by chromatography (SiO$_2$, 1/10=MeOH/CH$_2$Cl$_2$) to give the desired compound (2170 mg, 100%): $^1$H NMR (300 MHz, DMSO-d$_6$) δ 8.797 (t, J=5.0 Hz, 1H), 8.385 (t, J=6.0 Hz, 1H), 8.227 (9.6, 1H), 8.082 (t, J=5.9 Hz, 1H), 7.951 (d, J=9.0 Hz, 1H), 6.804 (s, 2H), 6.530 (s, 1H), 5.241 (s, 2H), 4.830 (m, 2H), 4.453 (dd, J=16.2, 7.2 Hz, 1H), 4.1–3.8 (m, 3H), 3.7–3.5 (m, 2H), 2.814 (dd, J=15.3, 5.4 Hz, 1H), 2.628 (dd, J=15.9, 8.6 Hz, 1H), 2.384 (dd, J=15.3, 9.0 Hz, 1H), 2.253 (dd, J=15.8, 6.3 Hz, 1H), 1.357 (s, 18H); $^{13}$C NMR (300 MHz, DMSO-d$_6$) δ 170.6, 169.9, 169.8, 169.3, 169.23, 169.16, 168.4, 148.3, 140.4, 134.8, 114.7, 112.6, 111.0, 80.1, 49.1, 48.8, 44.2, 42.4, 41.4, 37.6, 37.0, 27.7 (2C); LRMS (FAB) m/e calc'd for C$_{28}$H$_{41}$N$_6$O$_9$ (M+H$^+$): 605.2935, found 605.4.

III. Synthesis of Calix[4]arenetetracaboxylic acid

The synthesis of a preferred calixarene unit, calix[4]arenetetraacid, useful in practicing the present invention, is illustrated in FIG. 3, and discussed in detail hereinafter.

p-tert-Butylcalix[4]arene (HMY2809). A 2 L 4-neck flask with a mechanical stirrer was placed in an oil bath. To a mixture of p-tert-butylphenol (100 g, 665 mmol) and formalin (37% HCHO, 62.3 mL, 830 mmol) in the flask was added a solution of NaOH (1.2 g, 30 mmol) in water (5 mL). The mixture was heated up to 110°–120° C. with the top open to remove water. A pinkish solution thickened and became yellow solid after four hours. The oil bath was removed and the mixture was allowed to cooled down to r.t. Diphenyl ether (1000 g) was added and the mixture was warmed up to dissolve the yellow solid. Nitrogen was blown rapidly to remove water and the mixture became yellow solution. The mixture was refluxed for two hours and became dark brown color. The mixture was cooled down, added AcOEt (1000 mL), left overnight. The precipitation was collected on a Buchner funnel and washed with AcOEt (2×100 mL) and AcOH (3×200 mL). The cake was dried in vacuo to give the desired compound (61.4 g, 57%): $^1$H NMR (300 MHz, CDCl$_3$) δ 10.355 (s, 4H), 7.059 (s, 8H), 4.265 (d, J=13.2 Hz, 4H), 3.504 (d, J=13.5 Hz, 4H), 1.218 (s, 36H). For further details on synthesis of this type of unit, see Gutsche, C. D.; Iqbal, M.; Stewart, D. *J. Org. Chem.* 1986, 51, 742–745, incorporated in its entirety by reference herein.

Tetrahydroxycalix[4]arene (HMY2812). To a suspension of p-tert-butylcalix[4]arene (26.0 g, 40 mmol) and phenol (18.1 g, 192 mmol) in toluene (250 mL) was added AlCl$_3$ (28.0 g, 210 mmol) and the mixture was stirred at r.t. for one hour. The reaction mixture was poured into 0.2N HCl (500 mL) and the unsolved matter was filtered off. The organic layer was separated and evaporated. Upon the addition of MeOH (400 mL) precipitation formed and was collected on a Buchner funnel. The crude product was recrystallized from CHCl$_3$ and MeOH to give the titled compound as a pale yellow powder (12.8 g, 75%): $^1$H NMR (300 MHz, CDCl$_3$) δ 10.199 (s, 4H), 7.056 (d, J=7.5 Hz, 8H), 6.730 (t, J=7.5 Hz, 4H), 4.248 (broad s, 4H), 3.546 (broad s, 4H). For additional details on the synthesis of this compound, see Gutsche, C. D.; Lin, L.-G. *Tetrahedron* 1986, 42, 1633–1640, incorporated in its entirety by reference herein.

Tetrakis(butyloxy)calix[4]arene (HMY2813). 60% NaH (11.8 g, 295 mmol) was washed with hexanes (3×150 mL). To a suspension of the NaH in dry DMF (450 mL) was added tetrahydroxycalix[4]arene (14.8 g, 34.7 mmol) and the mixture was heated at 70° C. for ten minutes. The mixture was added 1-bromobutane (41.1 g, 300 mmol) and stirred at 70° C. for additional one hour. After cooled down to r.t., the mixture was quenched by the dropwise addition of MeOH (20 mL). After the removal of solvent by evaporation, water (1000 mL) was added and precipitation formed. The precipitation was collected on a glass filter and washed with MeOH (2×200 mL). The crude product was recrystallized from acetone to give the titled compound as white crystals (17.3 g, 77%): m.p. 115°–116°; $^1$H NMR (300 MHz, CDCl$_3$) δ 6.622 (m, 12H), 4.451 (d, J=13.2 Hz, 4H), 3.892 (t, J=7.4 Hz, 8H), 3.151 (d, J=13.2 Hz, 4H), 1.901 (quintet, J=7.5 Hz, 8H), 1.452 (hextet, J=7.5 Hz, 8H), 0.999 (t, J=7.4 Hz, 12H); HRMS m/e calc'd for C$_{44}$H$_{56}$O$_4$: 648.4177, found 648.4146; Analysis calc'd for C$_{44}$H$_{56}$O$_4$: C, 81.44; H, 8.70; found: C, 81.51; H, 8.65. For further details on the synthesis of this compound, see Conner, M.; Janout, V.; Regen, S. L. J. Org. Chem. 1992, 57, 3744–3746, incorporated in its entirety by reference herein.

Tetrakis(butyloxy)calix[4]arenetetracaboxaldehyde (HMY2824). To a solution of 1,1-dichloromethyl methyl ether (12.2 mL, 135 mmol) in dry CH$_2$Cl$_2$ (100 mL) was added TiO$_4$ (17.6 g, 160 mmol). A solution of tetrakis (butyloxy)calix[4]arene in dry CH$_2$Cl$_2$ (50 mL) was added to the solution above at −15° C. and the mixture was stirred at −15° C. for one hour and at r.t. overnight. The reaction was quenched with 1N HCl (150 mL) and the organic layer was diluted with CH$_2$Cl$_2$ (100 mL) and separated. The crude product solution was directly applied to a chromatography (SiO$_2$, first CH$_2$Cl$_2$, second 1/9=AcOEt/CH$_2$Cl$_2$, third 1/5= AcOEt/CH$_2$Cl$_2$) to give the titled compound (7.0 g, 92%): m.p. 246°–248°; $^1$H NMR (300 MHz, CDCl$_3$) δ 9.582 (s, 4H), 7.153 (s, 8H), 4.496 (d, J=13.8 Hz, 4H), 3.972 (t, J=7.4 Hz, 8H), 3.349 (d, J=14.1 Hz, 4H), 1.872 (quintet, J=7.5 Hz, 8H), 1.447 (hextet, J=7.5 Hz, 8H), 1.002 (t, J=7.4 Hz, 12H); HRMS m/e calc'd for C$_{44}$H$_{56}$O$_8$: 760.3975, found 760.4011; Analysis calc'd for C$_{44}$H$_{56}$O$_8$: C, 75.76; H, 7.42; found: C, 75.80; H, 7.43. For further details on the synthesis of analogous compounds, see Vreekamp, R. H. Thesis, University Twente, 1995, incorporated in its entirety by reference herein.

Tetrakis(butyloxy)calix[4]arenetetracaboxylic acid (HMY2830). To a solution of tetrakis(butyloxy)calix[4] arenetetracaboxaldehyde (3.81 g, 5.0 mmol) in CH$_2$Cl$_2$ (100 mL) and acetone (300 mL) was added a solution of H$_2$NSO$_3$H (4.27 g, 44 mmol) in water (25 mL). The mixture was added a solution of NaClO$_2$ (3.62 g, 40 mmol) in water (25 mL) and stirred at r.t. overnight. The reaction was quenched with 1N HCl (200 mL) and the organic solvents was evaporated. The white precipitate formed was collected on a glass filter and washed with water. The product was dried in vacuo over P$_2$O$_5$ (4.0 g, 100%): m.p. >360°; $^1$H NMR (300 MHz, DMSO-d$_6$) δ 12.348 (s, 4H), 7.309 (s, 8H), 4.326 (d, J=12.9 Hz, 4H), 3.901 (t, J=7.1 Hz, 8H), 3.384 (d, J=13.2 Hz, 4H), 1.843 (quintet, J=7.2 Hz, 8H), 1.420 (hextet, J=7.5 Hz, 8H), 0.961 (t, J=7.4 Hz, 12H); $^{13}$C NMR (300 MHz, DMSO-d$_6$) δ 166.8, 159.9, 134.4, 129.7, 124.6, 74.8, 31.8, 30.0, 18.8, 13.9; HRMS m/e calc'd for C$_{44}$H$_{56}$O$_{12}$: 824.3772, found 824.3801; Analysis calc'd for C$_{44}$H$_{56}$O$_{12}$: C, 69.89; H, 6.84; found: C, 69.55; H, 6.80. For further details on the synthesis of analogous compounds, see Vreekamp, R. H. Thesis, University Twente, 1995, incorporated in its entirety by reference herein.

IV. Synthesis of Calix[4]arenetetracyclicpeptide

A highly preferred embodiment of the invention comprises a new compound named calix[4]arenetetracyclicpeptide, a preferred synthesis route for which is illustrated in FIG. 4, and is discussed in detail hereinafter. It will now, of course, be readily appreciated that other synthesis routes are possible and that other similar compounds are possible, for example, those having more than four peptide loops and/or more than four arene groups in the calixarene scaffold. It is, of course, intended that these alternative embodiments fall within the full scope of the claims appended hereto, including any and all equivalents thereof.

Calix[4]arenetetracyclicpeptide (HMY2850). To a solution of tetrakis(butyoxy)calix[4]arenetetracarboxylic acid (86 mg, 0.10 mmol) and oxalyl chloride (254 mg, 2.0 mmol) in dry CH$_2$Cl$_2$ (10 mL) was added DMF (0.025 mL) through a silica gel filter and the mixture was stirred at room temperature for eight hours. The reaction mixture was evaporated in vacuo to obtain the acid chloride (102 mg). A solution of cyclic peptide (266 mg, 0.44 mmol) and DIEA (80 mg, 0.60 mmol) in dry CH$_2$Cl$_2$ (10 mL) was added to the evaporated residue. The mixture was stirred at room temperature for 14 hours. The reaction mixture was directly applied to preparative TLC (SiO$_2$, first 1/9=MeOH/CH$_2$Cl$_2$, later 1/4=MeOH/CH$_2$Cl$_2$) to obtain the desired compound as a yellow powder (281 mg, 89%): $^1$H NMR (300 MHz, DMSO-d$_6$) δ 10.100 (broad s, 4H), 8.951 (broad, 4H), 8.488 (broad, 4H), 8.254 (d, J=8.7 Hz, 4H), 8.092 (broad, 4H), 7.990 (m, 8H), 7.674 (s, 4H), 7.602 (s, 8H), 7.371 (s, 4H), 4.808 (m, 8H), 4.512 (m, 8H), 3.989 (m, 20H), 3.629 (m, 8H), 3.457 (m, 4H), 2.793 (m, 4H), 2.624 (m, 4H), 2.305 (m, 8H), 1.974 (m, 8H), 1.472 (m, 8H), 1.347 (m, 72H), 1.015 (t, J=8.4 Hz, 12H); $^{13}$C NMR (300 MHz, DMSO-d$_6$) δ 120.1, 117.8, 80.0 (2C), 75.0, 49.1, 48.8, 44.2, 42.3, 41.4, 37.5, 36.9, 31.9, 30.5, 27.6 (2C), 18.9, 14.0.

Calix[4]arenetetracyclicpeptide1 (HMY3005). The preceeding calix[4]arenetetracyclicpeptide (298 mg, 0.094 mmol) was added in TFA (3 mL) and dry CH$_2$Cl$_2$ (3 mL) and the mixture was stirred at r.t. for one hour. The mixture was evaporated under reduced pressure. The product was passed through anion exchange resin (Amberlite IRA-400(OH), water) and cation exchange resin (Amberlite IR 120 (plus), water) to remove ions. Water was lyophilized to give the titled compound (229 mg, 90%): $^1$H NMR (300 MHz, DMSO-d$_6$) δ 10.019 (s, 4H), 8.813 (s, 4H), 8.477 (s, 4H), 8.312 (d, J=8.7 Hz, 4H), 7.966 (m, 12H), 7.635 (s, 4H), 7.553 (s, 8H), 7.295 (s, 4H), 4.763 (m, 8H), 4.515 (m, 8H), 4.0–3.4 (m, 32H), 2.8–2.6 (m, 8H), 2.5–2.3 (m, 8H), 1.971 (m, 8H), 1.496 (m, 8H), 1.013 (t, 8.1H); $^{13}$C NMR (300 MHz, DMSO-d$_6$) δ 172.2, 171.7, 170.9, 170.4, 169.3, 168.5 (2C), 165.1, 159.0, 140.2, 138.8, 134.4, 134.2, 128.7, 128.3, 121.4, 119.9, 117.7, 75.0, 49.1 (2C), 44.3, 42.2, 41.3, 36.1 (2C), 31.9, 30.5, 18.9, 14.0.

D. Experiments Demonstrating the Binding Capability of Tetracyclicpeptide-Calix[4]arene Several experiments were conducted with a preferred embodiment of the present invention, in order to verify the usefulness thereof as a synthetic antibody capable of recognition of, and having binding affinity to, target proteins.

I. Tetracyclicpeptide-Calix[4]arene vs. Cytochrome c

Figure 8A:
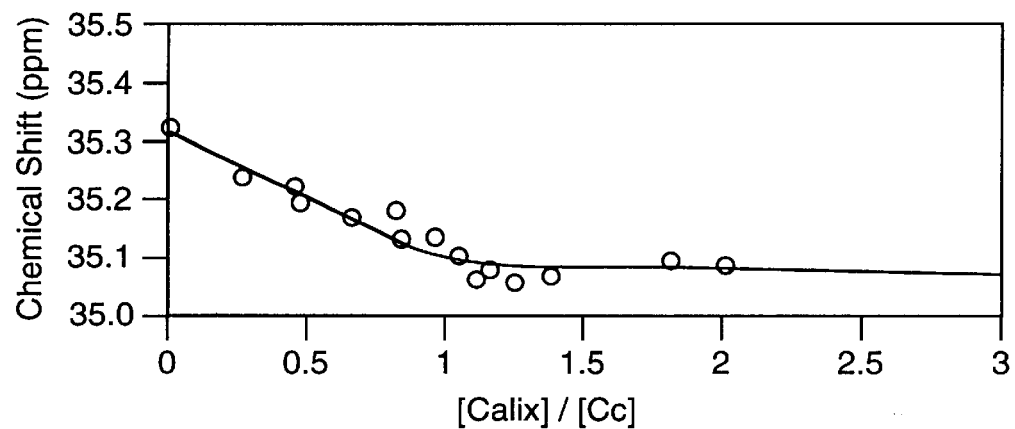
FIGS. 8A and 8B illustrate an NMR titration of 3.0 mM Cytochrome c with a preferred embodiment of the invention.
Figure 8B:
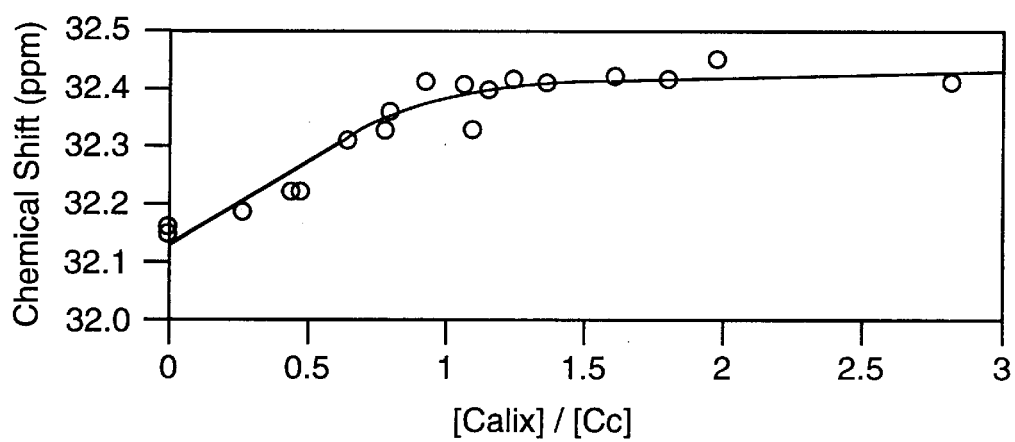

Horse Cytochrome c is an electron-transferring protein with a heme prosthetic group. The size of this protein is 12,384 Dalton and the surface is highly positively charged with lysine and arginine residues. For the X-ray crystal structure of Cytochrome c, see: Bushnell, G. W.; Louie, G. D.; Brayer, G. D. J. Mol. Biol. 1990, 214, 585. NMR titration of Cytochrome c with a preferred embodiment of the invention, designated 1 below, was performed under the condition described in FIG. 8 and two of the hyperfine region protons from heme in Cytochrome c, heme 8-CH$_3$ and heme 3-CH$_3$, were followed. Upon the addition of 1, 8-CH$_3$ moved downfield and 3-CH$_3$ moved upfield and both peaks became broad. The direction and the size of shifts are about the same as those of the titration between Cytochrome c and Cytochrome c peroxydase and peak broadening was also observed in the peroxydase titration. For NMR titration of cytochrome c and cytochrome-c peroxydase, see:

Satterlee, J. D.; Moench, S. J.; Erman, J. E. *Biochemica et Boiphysica Acta* 1987, 912, 87–97. FIG. 8 is consistent with 1:1 binding.

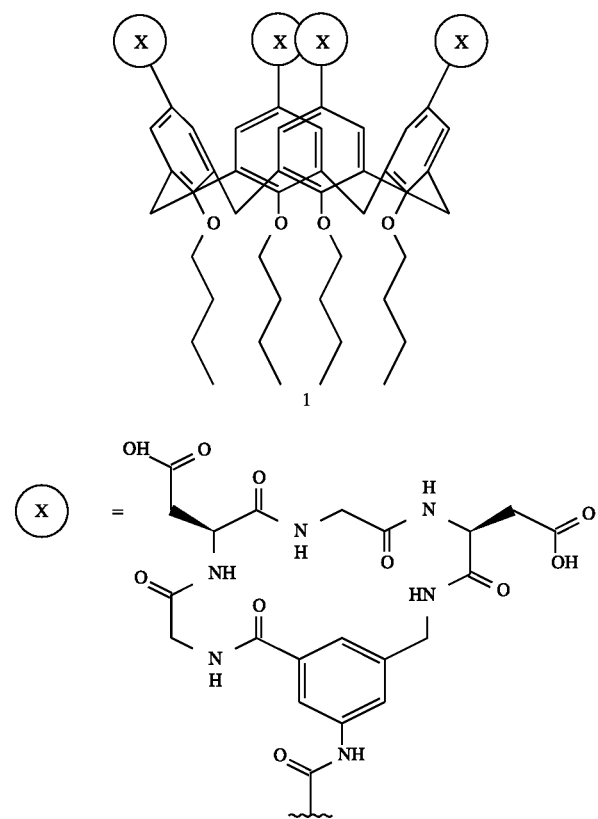

Figure 9:
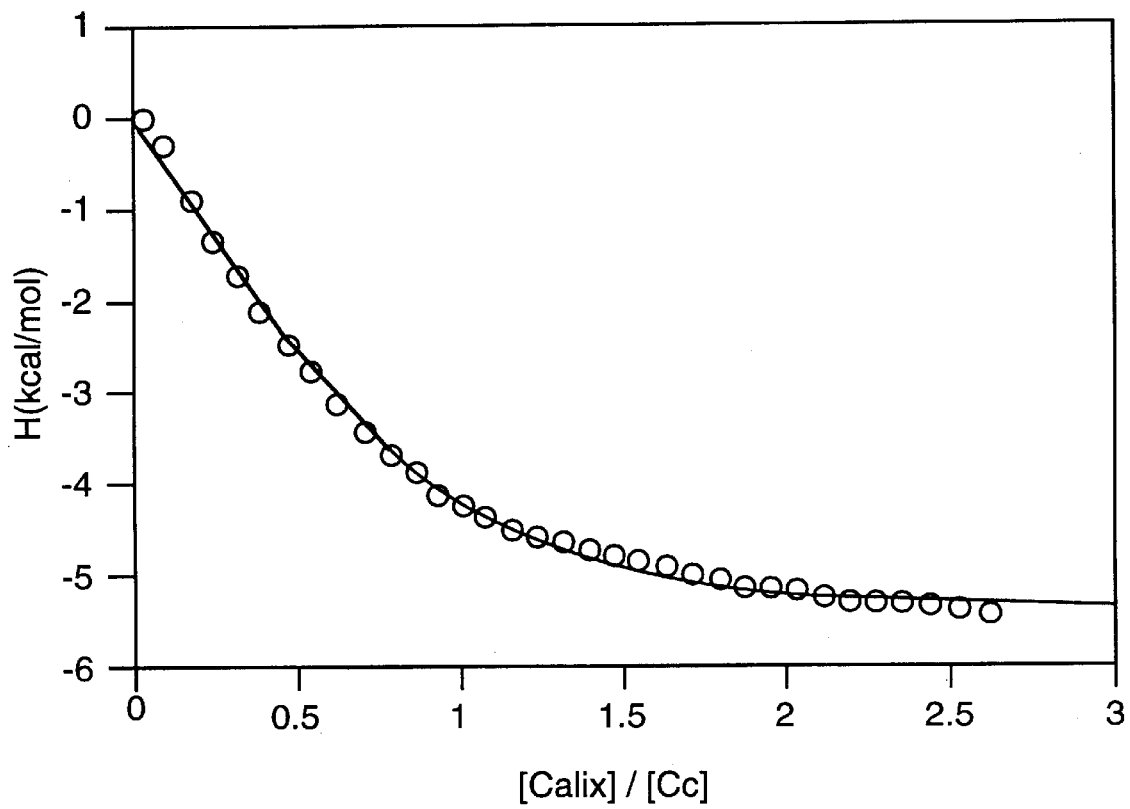
FIG. 9 illustrates a micro calorimetry titration of Cytochrome c with a preferred embodiment of the present invention.

Micro calorimetry titration of Cytochrome c with 1 was also performed (see FIG. 9). The association constant was calculated as $136000M^{-1}$ therefore $\Delta G=-7.0$ kcal/mol. As the enthalpy of the binding event is simulated as $-5.6$ kcal/mol, the entropy portion should be $-1.4$ kcal/mol. Therefore this binding is mainly enthalpy driven, presumably due to electrostatic interaction between lysine residues of Cytochrome c and aspartate residues of 1.

II. Tetracyclicpeptide-Calix[4]arene vs. Melittin

Melittin is an amphipathic bee venom lytic peptide consisting of 26 amino acid residues with 6 positive charges and no negative charges. For the structure of melittin, see: Terwillinger, T. C.; Eisenberg, D. *J. Biol. Chem.* 1982, 257, 6016–6022.

Figure 10:
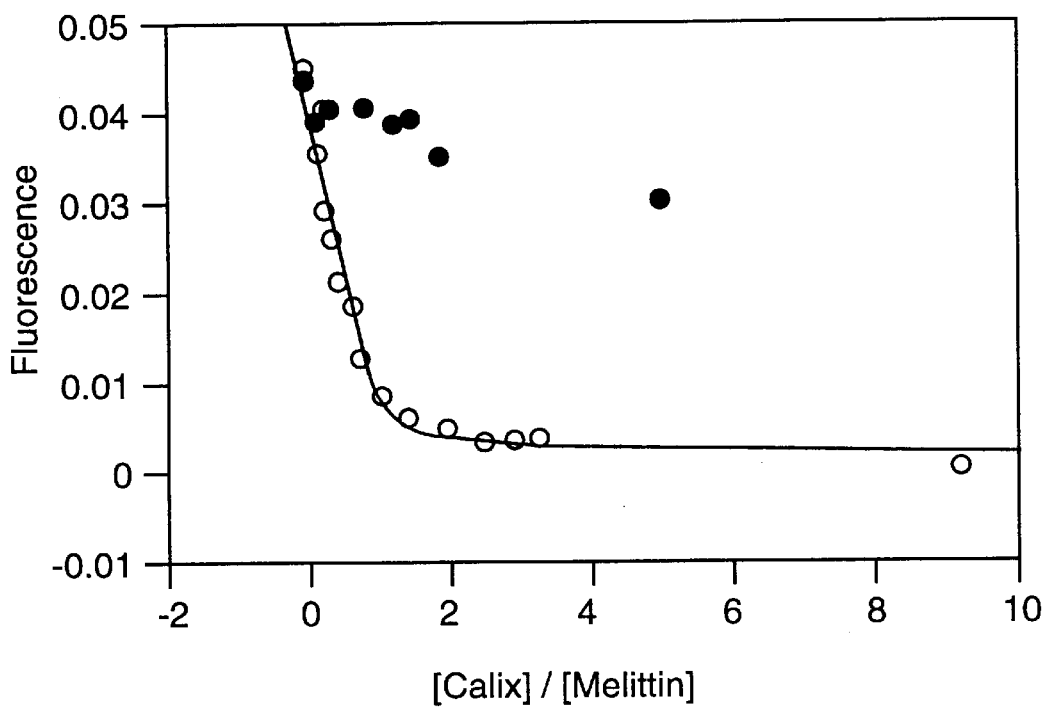
FIG. 10 illustrates a flourescence titration of 0.010 mM melittin with a preferred embodiment of the present invention.

Upon the fluorescence titration of melittin with 1, (for fluorescence study of lipid-melittin interaction, see: Dufourcq, J.; Faucon, J.-F. *Biochemica et Boiphysica Acta* 1977, 467, 1–11) the original melittin emission at 344 nm decreased and new peak at 452 nm appeared (Fluorescence at 452 nm was not shown) although the addition of 2 below did not effect the fluorescence of melittin as much (see FIG. 10).

Figure 11:
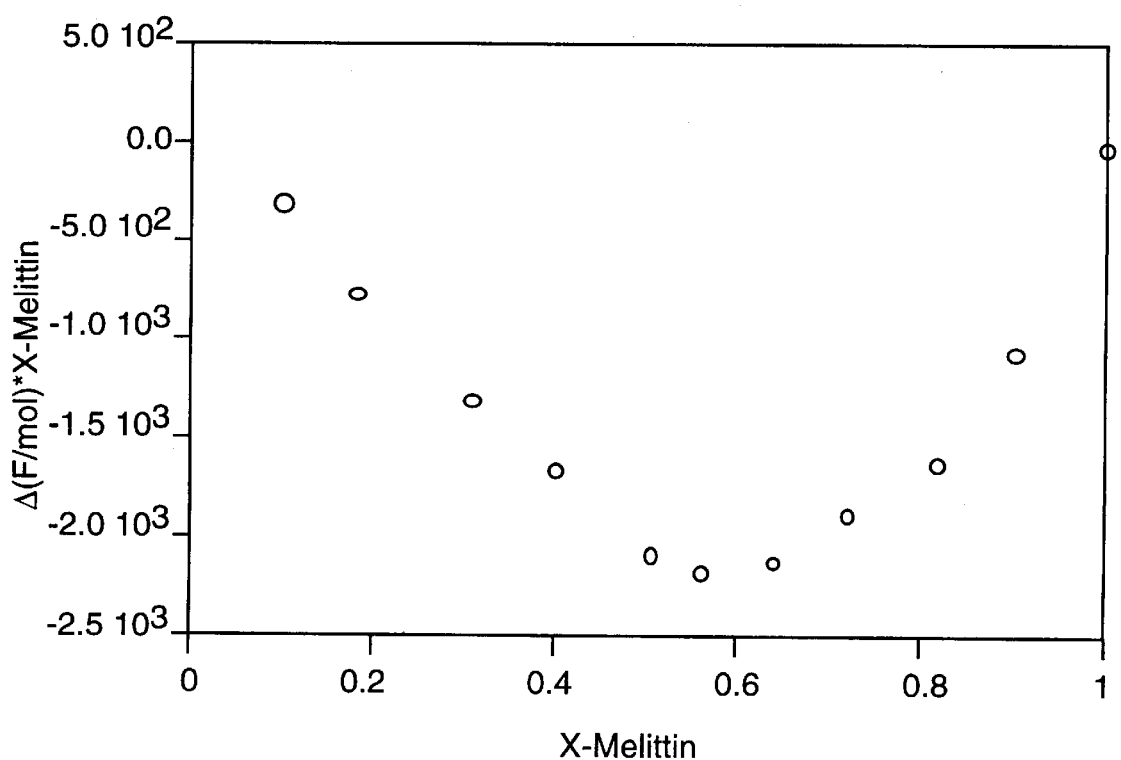
FIG. 11 illustrates a Job's plot of melittin with a preferred embodiment of the present invention.

This strongly indicates that in order to interact with melittin more than one cyclicpeptide has to be placed in vicinity. This is a strong evidence for the advantages of the preferred embodiments of the present invention, wherein more than one loop is attached to a scaffold and placed on the same side of the scaffold. Although a Job's plot (FIG. 11) shows that the stoichiometry is either 1:1 or 1:2, 1:2 seems to be the better model for this particular binding event as 1:1 model could not fit the binding curvature but 1:2 model could fit the curvature reasonably well with binding constant of $10^6 M^{-1}$ (calculated by doubling the concentration of 1 assuming no cooperativity between first and second binding events and same binding affinities for both).

Although the antibody mimic of the preferred embodiment includes an organic scaffold comprising a calixarene unit, it would, of course, be possible to use other organic and even inorganic scaffolds for this purpose. That is to say, though less preferred, it would be possible, for example, to link a plurality of aryl groups together in linear fashion, as the organic scaffold.

Furthermore, the preferred embodiment of the present invention comprises four arylcarboxylate groups linked together to form a macrocyclic ring. It would, however, be possible to link two through eight arylcarboxylate groups together in a macrocyclic ring to be used as inorganic scaffold for purposes of the present invention. It should be noted, however, that the linking of three said arylcarboxylate groups together would likely create a structure having too great of a strain to be stable. Additionally, greater than eight arylcarboxylate groups in a macrocyclic ring would also not likely be sufficiently stable. Furthermore, it is preferred to have more than about six to eight peptide loops on the antibody mimic for purposes of maintaining biological stability.

The preferred antibody mimics of the present invention have a molecular weight of approximately 3,000 Dalton or less which renders such antibody mimics sufficiently small to avoid the aforementioned problems of the prior art.

As previously discussed, it is preferred that the peptide loops each project from the same side of the organic scaffold to which each is attached. It is highly preferred, but not strictly necessary, that these loops project at an angle of no greater than about 60° with respect to any adjacent peptide loop linked to the scaffold, as illustrated in FIG. 6. This helps ensure that each peptide loop will be positioned so as to increase the likelihood of high binding affinity to any given antigen. Of course, for certain proteins it is possible that angles of greater than 60° would be acceptable.

In another embodiment, the multiple peptide loops can project as side chains from a molecular scaffold, preferably at an angle of no greater than about 180° with respect to one another.

We claim:

1. An antibody mimic comprising a calixarene organic scaffold to which a plurality of peptide loops are covalently linked.

2. The antibody mimic of claim 1 wherein each said peptide loop is linked to said calixarene unit with a linking group.

3. The antibody mimic of claim 1 wherein said linking group is selected from the group consisting of 3-aminomethyl-5-aminobenzamide, 3-aminophenylacetamide, 7-aminonaphthyl-1-carboxamide and functionally related derivatives thereof.

4. The antibody mimic of claim 1 wherein said calixarene group is formed from a plurality of arylcarboxylate groups linked at positions that are meta to the carboxylate portion of each arylcarboxylate group to form a macrocyclic ring.

5. The antibody mimic of claim 1 wherein said calixarene group comprises a plurality of benzene rings wherein the carbon atoms of each benzene ring are numbered such that position one is at the carbon atom linked to said linking unit and each of said benzene rings is linked to two other benzene rings in the calixarene unit at the three and five position such that a macrocyclic ring is formed.

6. The antibody mimic of claim 5 wherein said benzene rings are each part of a different arylcarboxylate, and said calixarene unit contains two, three, four, five, six, seven, or eight arylcarboxylate groups.

7. The antibody mimic of claim 6 wherein each of said arylcarboxylate groups is linked to at least one said peptide loop.

8. The antibody mimic of claim 7 wherein each arylcarboxylate group includes an alkyloxy portion, and said alkyloxy portions of said arylcarboxylate groups all project from the same side of said macrocyclic ring.

9. The antibody mimic of claim 8 wherein each arylcarboxylate group has linked thereto one peptide loop and each said peptide loop is para to the alkyloxy portion of the arylcarboxylate group to which it is linked.

10. The antibody mimic of claim 1 wherein said peptide loops project from the same side of said calixarene unit.

11. The antibody mimic of claim 10 wherein each said peptide loop projects at an angle of no greater than about 60° with respect to any other peptide loop linked to said scaffold.

12. The antibody mimic of claim 1 wherein said calixarene unit comprises a calix(4)arene tetraacid.

13. The antibody mimic of claim 12 wherein said antibody mimic has the general structure:

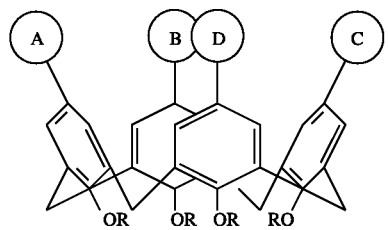

where R is selected from the group consisting of n-butyl, n-propyl, benzyl and A, B, C, and D each comprises a said peptide loop which may be the same or different with respect to one another.

14. The antibody mimic of claim 13 wherein each said peptide loop A, B, C, and D has the following general structure:

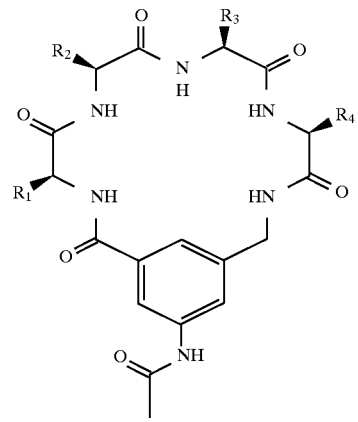

and wherein $R_1$, $R_2$, $R_3$, and $R_4$ may be the same or different and are selected from the group consisting of glycine, aspartate, lysine, arginine, histidine, phenylalanine, serine, alanine, leucine, tyrosine, tryptophan, and glutamic acid.

15. The antibody mimic of claim 14 wherein $R_1$ and $R_3$ are glycine and $R_2$ and $R_4$ are aspartate.

* * * * *

UNITED STATES PATENT AND TRADEMARK OFFICE
CERTIFICATE OF CORRECTION

PATENT NO.  : 5,770,380
DATED       : 23 June 1998
INVENTOR(S) : A. Hamilton, et al.

It is certified that error appears in the above-identified patent and that said Letters Patent is hereby corrected as shown below:

Column 1, following the title:

The invention described herein was made in the course of work performed under Grant No. GM53579 awarded by the National Institutes of Health. The United States Government has certain rights in this invention.

Signed and Sealed this

Twenty-second Day of June, 1999

Attest:

Q. TODD DICKINSON

*Attesting Officer*　　　*Acting Commissioner of Patents and Trademarks*